(12) United States Patent
Huang

(10) Patent No.: US 7,125,510 B2
(45) Date of Patent: Oct. 24, 2006

(54) MICROSTRUCTURE FABRICATION AND MICROSYSTEM INTEGRATION

(76) Inventor: Zhili Huang, 2004 Aspen Dr., Plainsboro, NJ (US) 08536

( * ) Notice: Subject to any disclaimer, the term of this patent is extended or adjusted under 35 U.S.C. 154(b) by 187 days.

(21) Appl. No.: 10/364,236

(22) Filed: Feb. 11, 2003

(65) Prior Publication Data

US 2003/0214057 A1 Nov. 20, 2003

Related U.S. Application Data

(60) Provisional application No. 60/380,607, filed on May 15, 2002.

(51) Int. Cl.
  *B29C 45/40* (2006.01)
  *B29C 45/03* (2006.01)
  *B29C 45/14* (2006.01)
(52) U.S. Cl. ............ 264/225; 264/221; 264/299; 264/328.1
(58) Field of Classification Search ............ 264/328.1, 264/225, 220, 221, 226, 335
See application file for complete search history.

(56) References Cited

U.S. PATENT DOCUMENTS

| | | | |
|---|---|---|---|
| 5,450,751 A * | 9/1995 | Putty et al. .............. 73/504.18 |
| 5,965,237 A | 10/1999 | Bruin et al. | |
| 6,033,202 A | 3/2000 | Bao et al. | |
| 6,136,212 A * | 10/2000 | Mastrangelo et al. ......... 216/49 |
| 6,238,538 B1 * | 5/2001 | Parce et al. ................. 204/600 |
| 6,297,072 B1 | 10/2001 | Tilmans et al. | |
| 6,511,463 B1 * | 1/2003 | Wood et al. ................ 604/272 |
| 6,663,820 B1 * | 12/2003 | Arias et al. ................... 264/496 |
| 6,679,471 B1 * | 1/2004 | Domeier et al. .............. 249/60 |
| 6,692,680 B1 * | 2/2004 | Lee et al. ..................... 264/485 |
| 2001/0054778 A1 | 12/2001 | Unger et al. | |

OTHER PUBLICATIONS

Michael L. Chabinyc et al. "An Integrated Fluorescence Detention System in Poly(dimethylsiloxane) for Microfluidic Applications". Anal. Chem. 73:4491-4498, 2001.
Hou-Pu Chou et al. "Integrated Elastomer Fluidic Lab-on-a-chip—Surface Patterning and DNA Diagnostics". Proceeding of the Solid State Actuate and Sensor Workshop, Hilton Head, South Carolina, 2000.
Zhili Huang et al. "A method for UV-bonding in the fabtication of glass electrophoretic microchips". Electrophoresis 22:3924-3929, 2001.
J. Cooper McDonald et al. "Fabrication of a Configurable, Single-use Microfluidic device". Anal. Chem. 73:5645-5650, 2001.
P. M. Martin et al. "Laminated plastic microfluidic components for biological and chemical systems". J. Vac. Sci. Technol. A 17(4):2264-2269, Jul./Aug. 1999.
Stephen R. Quake et al. "From Micro- to Nanofabrication with Soft Materials". Science 290:1536-1540, Nov. 24, 2000.
J. D. Trumbull et al. "Integrated Microfabricated Fluidic Systems and NMR Spectroscopy". IEEE Transactions on Biomedical Engineering 47(1): 3-7, Jan. 2000.

(Continued)

Primary Examiner—Christina Johnson
Assistant Examiner—Monica A Huson
(74) Attorney, Agent, or Firm—Fish & Richardson P.C.

(57) ABSTRACT

Fabrication of a microstructure device includes assembling a mold component and a mold body to form a device mold for the microstructure device. The microstructure device is cast from the device mold, then the mold component is removed from the microstructure device. The microstructure device is then released from the mold body.

48 Claims, 25 Drawing Sheets

OTHER PUBLICATIONS

Aimin Tan et al. "Rapid fabrication of microfluidic devices in poly(dimethylsiloxane) by photocopying". Lab on a Chip 1:7-9, 2001.

Marc A. Unger et al. "Monolithic Microfabricated Valves and Pumps by Multilayer Soft Lithography". Science 288:113-116, Apr. 7, 2000.

* cited by examiner

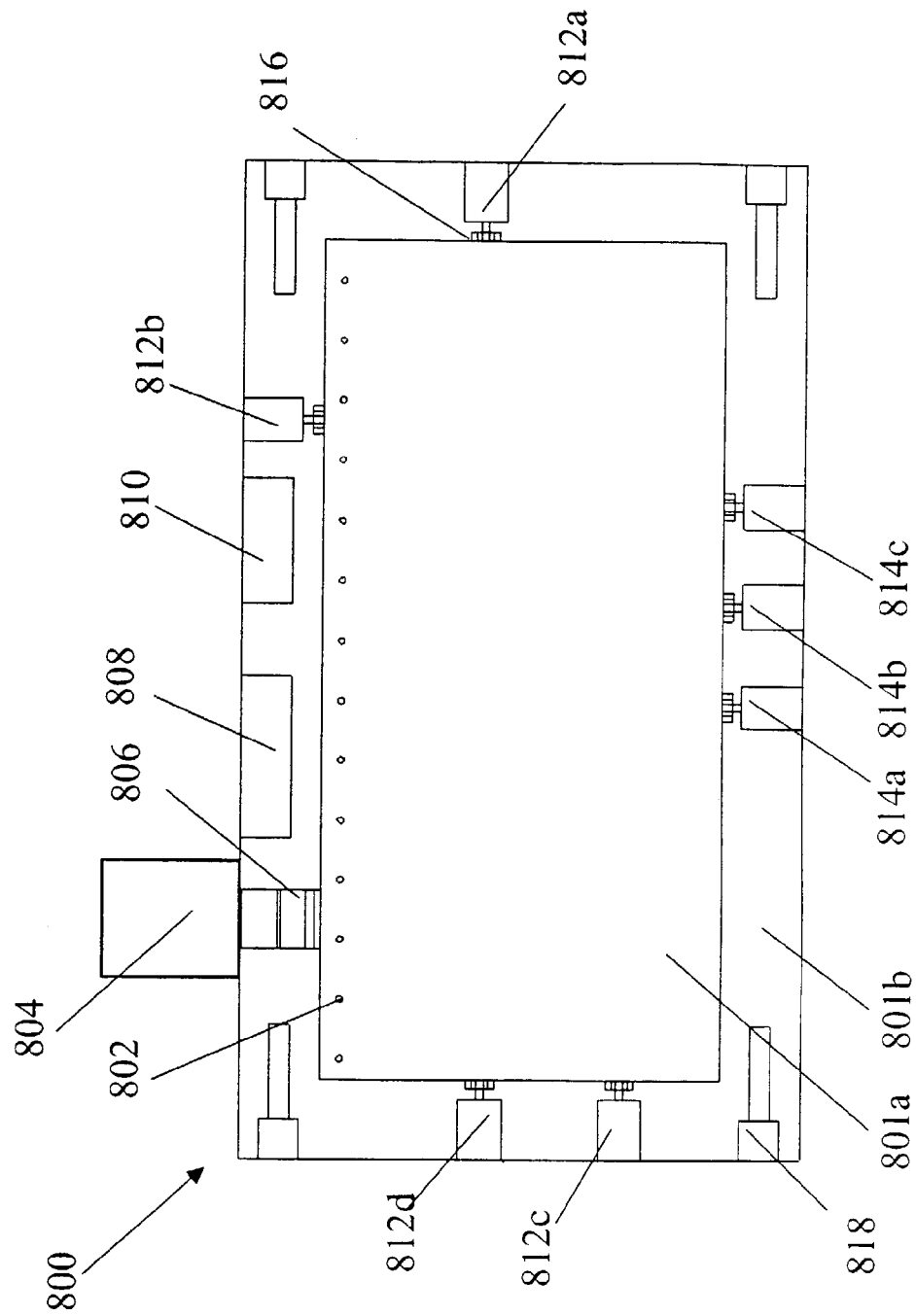

MICROSTRUCTURE FABRICATION AND MICROSYSTEM INTEGRATION

CROSS-REFERENCE TO RELATED APPLICATIONS

This application claims priority to U.S. Provisional Patent Application Ser. No. 60/380,607 by Zhili Huang entitled "MICROSTRUCTURE FABRICATION AND SYSTEM INTEGRATION," filed May 15, 2002.

TECHNICAL FIELD

This invention relates to microstructure fabrication and microsystem integration.

BACKGROUND

A micro total analysis system ("µTas", also called a lab-on-a-chip system) integrates microfluidics components with microelectromechanical systems (MEMS) into a single miniaturized device. The micro total analysis system can be used to perform chemical and biological analyses, such as capillary electrophoresis (CE), flow cytometry, liquid chromatography (LC), and mass spectroscopy (MS). The micro total analysis system can also be used to synthesize chemicals and drugs, and carry out clinical analyses. The micro total analysis system includes microfluidic devices that are used to manipulate and analyze fluid samples. Examples of microfluidic devices include microchannels, microvalves, micropumps, and micromixers. Because the components of the µTas are integrated together, only small amounts of fluid and sample are required for the analyses. This improves system performance and reduces sample, reagent, and analysis costs.

SUMMARY

In general, in one aspect, the invention features a method of fabricating a microstructure device, including assembling a mold component and a mold body to form a device mold for the microstructure device, casting the microstructure device from the device mold, removing the mold component from the microstructure device, and releasing the microstructure device from the mold body.

Embodiments of the invention may include one or more of the following features. Casting the microstructure device comprises pouring or injecting a liquid polymer into the device mold. The method may include combining the liquid polymer with a filler material or reinforcement particles. The liquid polymer may include polyurethane, polydimethylsiloxane, polycarbonate, polypyrrole, resin, Teflon resin, epoxy, polymeric rubber, or polymeric plastic.

The mold component may include a reversible material that changes from a solid form to a liquid form or from a liquid form to a solid form depending on changes in one or more environment conditions. Removing the mold component may include changing the one or more environment conditions so that the reversible mold component changes from a solid form to a liquid form. Removing the mold component may include applying a centrifugal force to draw the mold component in liquid form away from the microstructure device. Removing the mold component may include using a suction force to draw the mold component in liquid form away from the microstructure device.

The mold component may include a material that changes from a solid form to a gaseous form or from a gaseous form to a solid Finn depending on changes in one or more environment conditions. Removing the mold component may include changing the one or more environment conditions so that the mold component changes from a solid form to a gaseous form. The mold component may include a soluble material that can be cast into a predefined shape as defined by a mold and later be dissolved in a solvent. Removing the mold component may include flushing the mold component out from the microstructure device with a solvent that dissolves the mold component.

The mold component may include wax, gel, fusible alloy, eutectic alloy, resin, lipid, or ammonium salt. The mold component may have structures having a dimension less than 5 millimeters. The mold component may have a shape that is complementary of a structure of the microstructure device after the mold component is removed from the microstructure device. The mold component may include an elongated mold component having a same dimension and shape as a channel in the microstructure device after the mold component is removed from the microstructure device.

The method may include fabricating the mold component by using a component mold. Fabricating the mold component may include pouring a material in a liquid form into the component mold, and changing one or more environment conditions so that the material changes to a solid or gel form. The component mold may have a cavity having a shape that is substantially the same as a shape of the mold component, the cavity being connected to an exterior of the component mold through an opening, wherein fabricating the mold component may include injecting a material in a liquid form into the cavity through the opening, and changing one or more environment conditions so that the material changes to a solid or gel form. The component mold may have a cavity having a shape that is substantially the same as a shape of the mold component, wherein fabricating the mold component may include compressing a material in powder form into the cavity to form the mold component.

In general, in another aspect, the invention features a method that includes assembling a set of mold components and a mold body to form a device mold for a microstructure device, casting the microstructure device from the device mold, and removing the set of mold components from the microstructure device.

Embodiments of the invention may include one or more of the following features. Casting the microstructure device may include pouring or injecting a liquid polymer into the device mold. The set of mold components may include a first mold component and a second mold component, the first mold component having a shape configured so that a first chamber is formed in the microstructure device when the first mold component is removed from the microstructure device, the second mold component having a shape configured so that a second chamber is formed in the microstructure device when the second mold component is removed from the microstructure device. The first and second mold components may be spaced at a distance when the device mold is assembled so that a flexible membrane is formed in the microstructure device between the first and second chambers when the first and second mold components are removed from the microstructure device.

The set of mold components may include a first elongated mold component and a second elongated mold component, the first elongated mold component having a diameter or dimension smaller than the second elongated mold component, the second elongated mold component having an opening which has same dimension as the cross section of the first elongated mold component, and assembling the device mold may include inserting the first elongated mold component through the opening in the second elongated mold component to form an intersection.

The set of mold components may include an elongated mold component and a cylinder, the cylinder having a passageway with a dimension substantially the same as a dimension of the elongated mold component, and assembling the device mold may include partially inserting the elongated mold component into the passageway.

The set of mold components may include a castable mold component and an elongated mold component, the castable mold component having a shape configured to form a cavity in the microstructure device, the elongated mold component having a shape configured to form a channel in the microstructure device, the castable mold component having a recess structure for receiving an end of the elongated mold component, the recess structure having means to prevent the castable mold component from moving relative to the elongated mold member when the device mold is assembled.

The elongated mold component may have a first end and a second end, the mold body having a side wall with a hole, wherein assembling the device mold may include inserting the first end of the elongated mold component into the recess structure of the castable mold component, and inserting the second end of the elongated mold component through the hole of the side wall of the device mold.

The set of mold components may include a castable mold component having a shape suitable for forming a cavity and an elongated mold component suitable for forming a channel connecting the cavity in the microstructure device, wherein assembling the device mold may include inserting the elongated mold component through a hole positioned on a side wall of the mold body, the elongated mold component supporting and aligning the castable mold component at a predefined position relative to the mold body.

The set of mold components may include a post and an elongated mold component, the post supporting the elongated component at a predetermined position relative to the mold body when the device mold is assembled.

In general, in another aspect, the invention features a method of fabricating a microstructure device. The method includes fabricating a device mold by connecting a set of mold components and to mold body and connecting a set of functional components to the mold body, casting the microstructure device from the device mold, and removing the set of mold components from the microstructure device while retaining the functional components in the microstructure device.

Embodiments of the invention may include one or more of the following features. Casting the microstructure device may include pouring or injecting a liquid polymer into the device mold. The set of mold components may include a castable mold component, the set of functional components may include an electrode having a tip, wherein fabricating the device mold may include embedding a tip of the electrode into one of the castable mold components so that the tip of the electrode is surrounded by the castable mold component, and wherein removing the castable mold component from the microstructure device exposes the tip of the electrode to a cavity in the microstructure device.

The set of castable mold components may include an elongated mold component, the set of functional components may include an electrode having a structure that defines a hole, wherein fabricating the device mold may include inserting the elongated mold component through the hole in the electrode. The set of mold components may include an elongated mold component that defines a conduit in the microstructure device, the method further including coating a surface of the conduit with a material having a refractive index lower than a refractive index of a liquid material used for filling the conduit.

In general, in another aspect, the invention features an apparatus that includes a microdevice body having a structure that defines a channel to allow passage of a fluid, an electrical component to interact with a portion of the liquid, a portion of the electrical component being embedded in the microdevice body, and an optical component to generate, transmit, or receive light that interacts with a portion of the liquid, a portion of the optical component being embedded in the microdevice body such that the microdevice body and the optical component and the electrical component form an integrated unit.

Embodiments of the invention may include one or more of the following features. The microdevice body may be substantially made of polymer. The apparatus may include a platform for supporting the electrical component and the optical component at predetermined positions. The platform may include a circuit board. The apparatus may include a device mold for casting the microdevice body. The apparatus may include a controller that is integrated with the microdevice body to control the electrical component.

The structure of the microdevice body may define a chamber connected to the channel, the electrical component may include a heater integrated with the microdevice body for heating a liquid in the chamber, the heater being controlled by the controller. The microcontroller may control the heater to heat the liquid in the chamber according to a predefined protocol to facilitate a polymerase chain reaction.

The optical component may include an optical waveguide. The optical component may include an optical sensor. The structure of the microdevice body may define a chamber, and the apparatus may include a valve to open or close the channel, the valve including a diaphragm made of shape memory alloy.

The structure of the microdevice body may define a fluid inlet, a chamber, and an opening between the fluid inlet and the chamber, the fluid inlet having a shape such that a fluidic pressure in a direction from the inlet towards the chamber tends to cause the opening to remain open, whereas a fluidic pressure in a direction from the chamber towards the inlet tends to close the opening.

The structure of the microdevice body may define a fluid inlet and a chamber, the fluid inlet has a funnel shape that extends into the chamber, the fluid inlet and the chamber being separated by a flexible membrane having a funnel shape having a larger opening that tapers into a smaller opening that connects the fluid inlet to the chamber.

In general, in another aspect, the invention features a microfluidic system that includes a microfluidic device having fluidic components, and a cassette having interfaces for interfacing the fluidic components.

Embodiments of the invention may include one or more of the following features. The microfluidic device may include pneumatic components. The cassette may include pneumatic interfaces configured to be coupled to the pneumatic components in the microfluidic device. The microfluidic device may include electrical components. The cassette may include electrical interfaces configured to be coupled to the electrical components in the microfluidic device.

In general, in another aspect, the invention features an apparatus that includes a device mold that includes a mold body, removable mold components, and functional components, the mold body and the removable mold components and the functional components being connected to define a space within the device mold for casting a microstructure device, the removable components including material that can be removed from the microstructure device after the microstructure device is cast, the functional components being integrated with the microstructure device after the microstructure device is cast.

Embodiments of the invention may include one or more of the following features. The removable mold components may include a first set of mold components and a second set of mold components, the first set of mold component having shapes configured to form chambers when the first set of mold component are removed from the microstructure device, the second set of mold components having shape configured to form channels when the second set of mold components are removed from the microstructure device, the first and second sets of mold components being positioned relative to one another when connected to form the device mold such that the chambers and channels in combination form a component of a peristaltic pump.

The mold body may include a bottom wall and a side wall, the side wall defining a hole that is positioned at a predetermined distance from the bottom wall, the hole receiving an end of one of the removable mold components, the predetermined distance selected so that the removable mold component is disposed at a predefined position relative to the mold body within the device mold.

Other features, objects, and advantages of the invention will be apparent from the description and drawings, and from the claims.

DESCRIPTION OF DRAWINGS

FIG. 25 shows a cassette having electrical, optical, and fluidic interfaces for the microfluidic device of FIG. 14.

DETAILED DESCRIPTION

The following definitions will be used in the description below:

The term "reversible material" refers to a material that is in solid state at a certain temperature, but changes to liquid state upon changes in the environment condition(s), such as when heated. The liquid state reversible material changes back to solid state when the environment condition(s) change in reverse direction, such as when the temperature lowers back to a certain degree. Examples of reversible materials are gel, fusible alloy, eutectic alloy, and resin.

The term "soluble material" refers to a lipid material that is in solid state at room temperature, but is soluble when upon contact with a solvent. Examples of soluble materials are soap, wax, sterols, and triglycerides.

The term "sublimable material" refers to a material that is in solid state at a certain temperature, but changes to vapor upon changes in the environment condition(s), such as when heated or when the environment pressure is reduced. The vapor state reversible material changes back to solid state (usually in powder form) when the environment condition(s) change in reverse direction, such as when the temperature lowers back to a certain degree. An example of sublimable material is ammonium salt, such as ammonium chloride ($NH_4Cl$) that completely decomposes into ammonia ($NH_3$) and hydrogen chloride (HCl) at 30° C. and 1.3 mbar.

The term "castable mold component" refers to a mold component made from one or more reversible, soluble, or sublimable materials. A castable mold component is molded to a certain shape that is a complementary of a microstructure to be fabricated inside a microfluidic device. A castable mold component can be removed from the microfluidic device after the microfluidic device is fabricated.

The term "elongated mold component" refers to a mold component having an elongated shape, such as a wire, a rod, or a sheet. A sheet may have a high aspect ratio in which the width and length are larger than the thickness. An elongated mold component can be made from steel, plastic, or silicon. An elongated mold component can also be a castable mold component that is cast from a mold having an elongated inner cavity.

Figure 1:
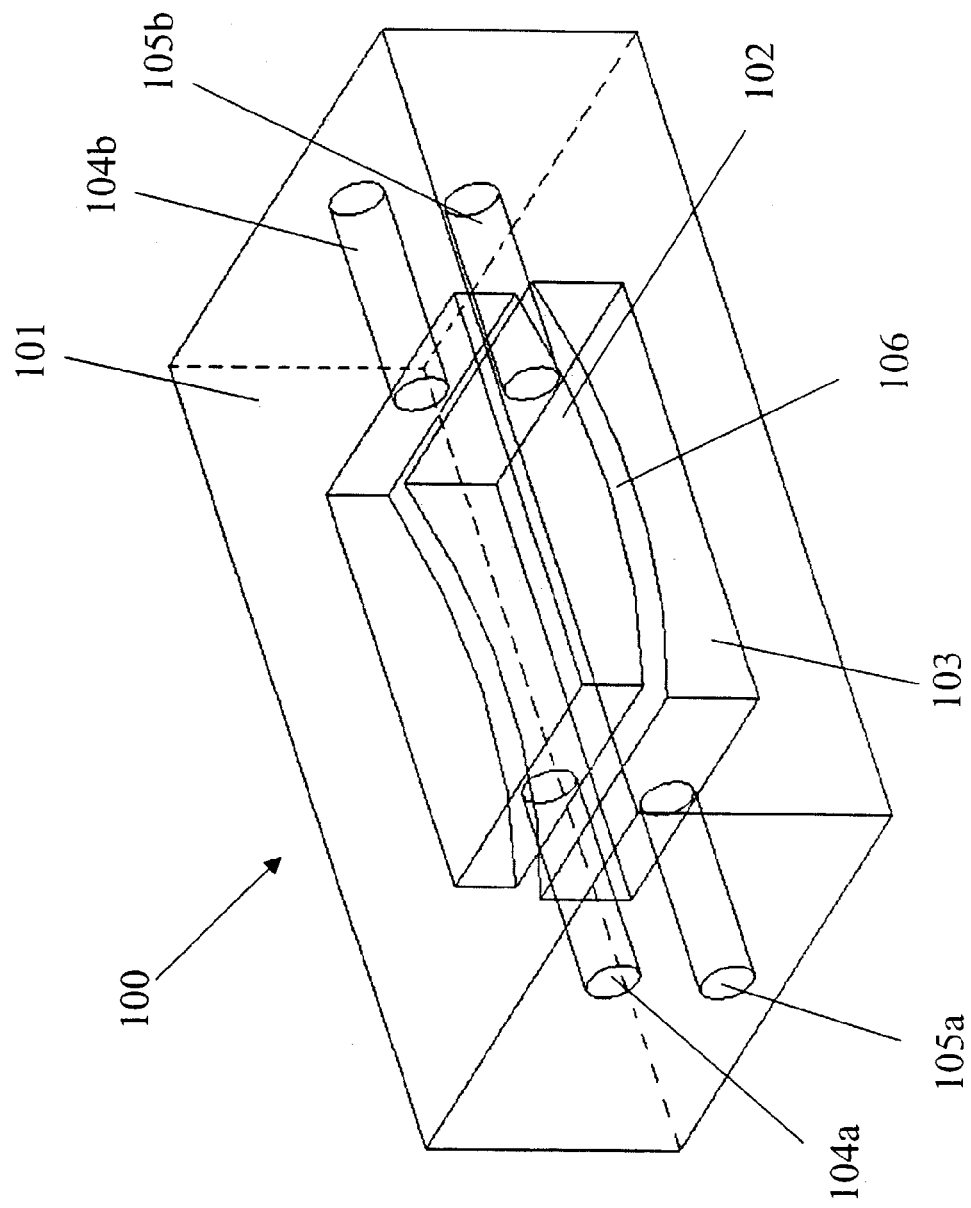
FIG. 1 shows a perspective view of a multi-chamber microdevice.
Figure 2:
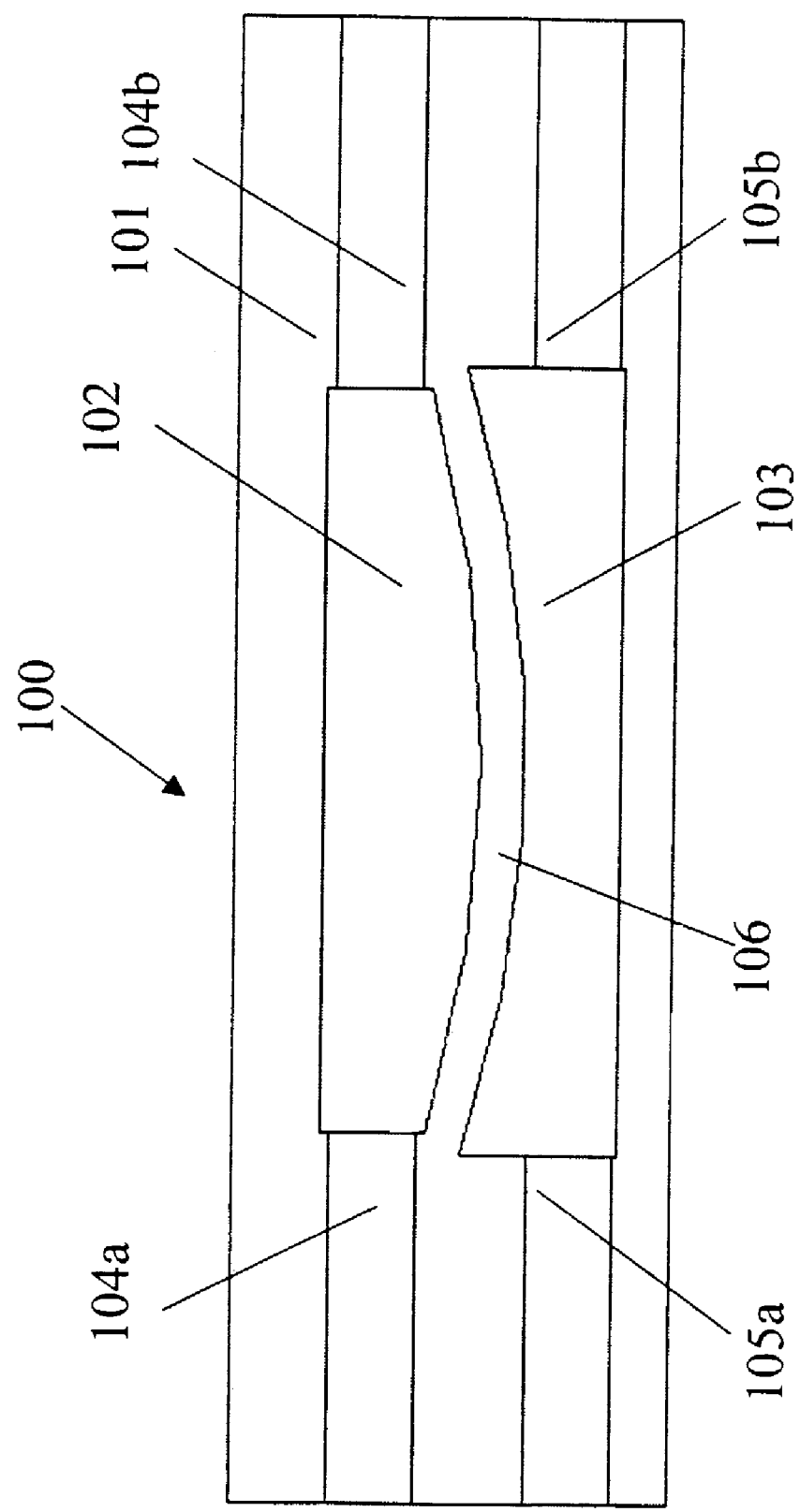
FIG. 2 shows a front view of the multi-chamber microdevice.
Figure 3:
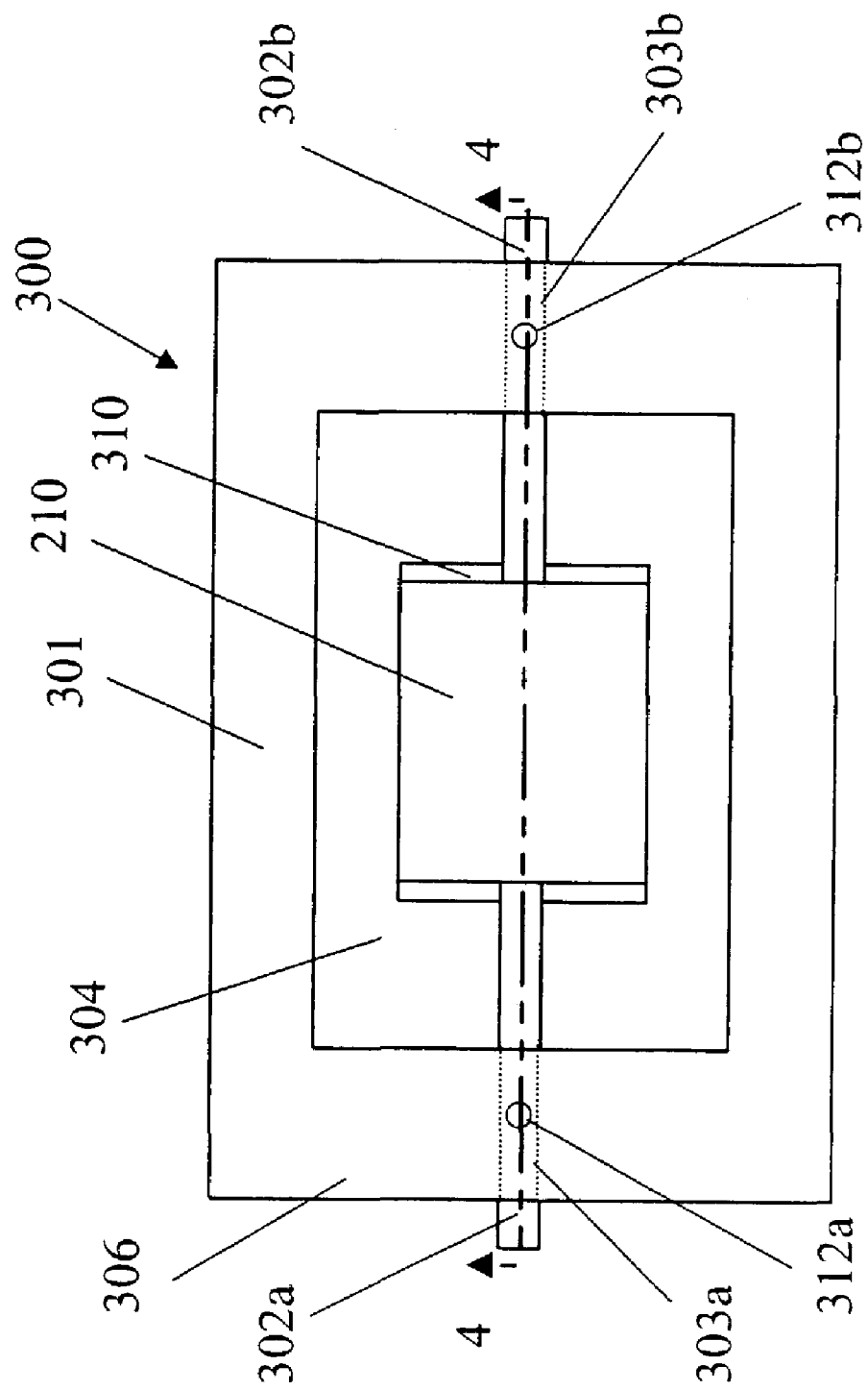
FIG. 3 shows a top view of a device mold used to cast the multi-chamber microdevice.
Figure 4:
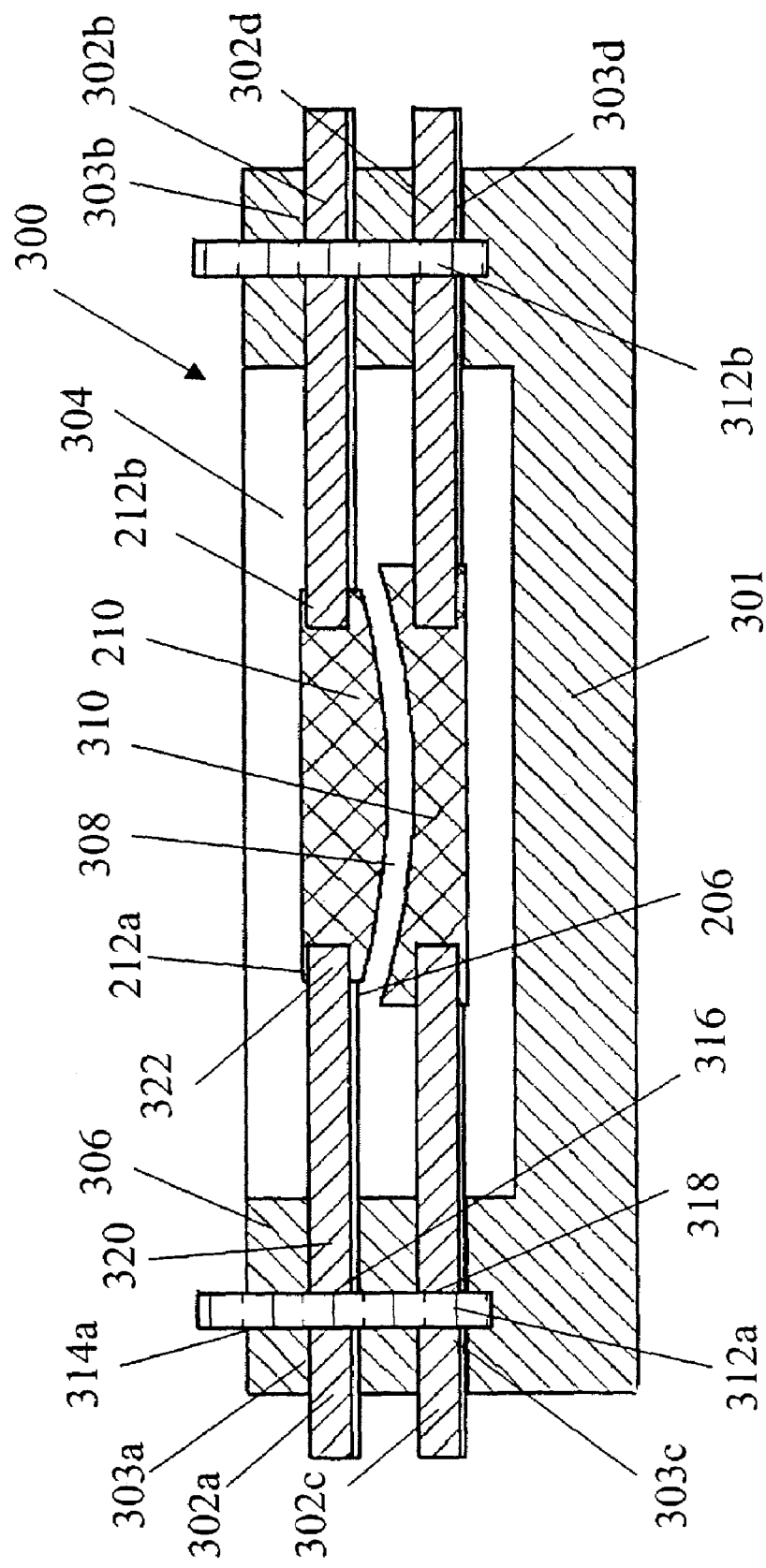
FIG. 4 shows a cross sectional views of the device mold used to cast the multi-chamber microdevice.

FIGS. 1 and 2 show perspective and front views, respectively, of a multi-chamber microdevice 100. FIG. 3 shows a top view of a device mold 300 used to cast the multi-chamber microdevice 100. FIG. 4 shows a cross sectional view of device mold 300 along a plane 8 in FIG. 3.

Referring to FIGS. 1–4, multi-chamber microdevice 100 is cast from the device mold 300. Device mold 300 is formed by assembling a mold body 301 with two castable mold components (210 and 310), and four elongated mold components (302a, 302b, 302c, and 302d). Liquid polymer is poured into a space 304 formed between mold body 301 and the mold components (210, 310, 302a–302d). When the liquid polymer is cured, the elongated mold components (302a–302d) are pulled out from the device mold 300.

In one example, the castable mold components are made of reversible materials. Device mold 300 is heated so that the reversible material melts into liquid state. The melted reversible materials can be removed from the microdevice 100 by vacuum suction or by applying a centrifugal force. Pressurized liquid or gas may also be used to flush out the melted reversible materials.

In another example, the castable mold components are made of sublimable materials. Microdevice 100 is heated to a sublimating temperature of the mold components so that the sublimable material evaporates and is separated from the microdevice 100.

In yet another example, the castabable mold components are made of soluble materials. A solvent can be used to flush the mold components so that the mold components dissolve in the solvent, which is removed by suction.

In the above examples, when the mold components are removed, an upper chamber 102, a lower chamber 103, and channels 104a, 104b, 105a, and 105b are formed in multi-chamber microdevice 100. Microdevice 100 is subsequently released from the mold body 301.

Mold body 301 can be made of steel or plastic.

Examples of liquid polymers are polyurethane, polydimethylsiloxane (PDMS), polycarbonate, polypyrrole, resin, Teflon resin, epoxy, polymeric rubber, or polymeric plastic. Liquid polymers can be solidified by mixing a polymer base and a curing agent at a certain ratio, for example, 10:1 for PDMS mixing. The polymerization time is about several hours at a certain temperature. For example, the polymerization time is 48 hours at room temperature, and 20 minutes at 100° C. for Sylgard 184 Silicone Elastomer from Dow Corning. After polymerization, the liquid polymer solidifies and forms a microstructure having features that accurately reproduces features of the device mold 300.

Fillers or reinforcement particles can be added to the liquid polymers to modify the properties of the solidified polymer. The properties that can be modified by the addition of fillers or reinforcement particles include hardness, density, impact strength, melting temperature, chemical resistance, and abrasion resistance, thermal conductivity, electrical conductivity, and electromagnetic interference shielding.

Referring to FIG. 4, device mold 300 is formed by assembling mold body 301 with mold components 210, 310, 302a–302d, 312a, and 312b. Mold components 210 and 310 define the shape of upper chamber 102 and lower chamber 103, respectively. Mold component 210 is supported by mold members 302a and 302b at a predefined position relative to mold body 301. Mold component 310 is supported by mold members 302c and 302d at a predefined position relative to mold body 301. Mold components 302a and 302b have elongated shapes (e.g., like rods) and define the shapes of channels 104a and 104b, respectively. Mold components 302c and 302d have elongated shapes (e.g., like rods) and define the shapes of channels 105a and 105b, respectively.

A portion 320 of mold component 302a is inserted through a hole 303a formed in a sidewall 306 of mold body 301. An end 322 of mold component 302a is inserted into a recessed structure 212a of mold component 210. Mold components 302b–302d are connected to mold body 301 and mold components 210 and 310 in like manner. A set rod 312a is inserted through a hole 314a of mold body 301, a hole 316 of mold component 302a, and a hole 318 of mold component 302c. Rod 312a prevents mold components 302a and 302c from moving relative to body mold 301. Likewise, a set rod 312b prevents mold components 302b and 302d from moving relative to body mold 301. Recess structure 212a has a ridge structure 214a, and the end 322 of mold component 302a has a groove structure 206a that is complementary of the ridge structure 214a. Ridge structure 214a and groove structure 206a prevent mold components 210 and 302a from moving relative to one another. Similar structures prevent mold components 210 and 302b; and mold components 310, 302c, and 302d from moving relative to one another.

In one example, mold components 210, 310, and 302a–302d are all made of reversible materials. Rods 312a and 312b may be made of the same material as mold body 301. After liquid polymer is poured into device mold 300 and cured, rods 312a and 312b are pulled away from device mold. The mold components are melted and removed by suction. In this example, mold components 302a–302d can have bending or winding shapes (e.g., such as shapes having multiple U-turns), as long as they are sufficiently rigid to support mold components 210 and 310.

In another example, mold components 310 and 210 are made of reversible, soluble, or sublimable materials, while mold components 302a–302d and the rods 312a and 312b are made of the same material as mold body 301 (e.g., steel or plastic). After liquid polymer is poured into device mold 300 and cured, rods 312a and 312b are pulled away from device mold 300. Then, mold components 302a–302d are pulled away from device mold 300, forming channels 104a, 104b, 105b, and 105b. Mold components 310 and 210 are dissolved by a solvent or removed by changing the environment conditions so that castable mold components 210 and 310 change to liquid or vapor state. In this example, mold components 302a–302d are straight or curved with a constant curvature so that mold components 302a–302d may be pulled out of device mold 300 after the liquid polymer is cured.

To remove the mold components made of reversible materials, after the mold components are melted and change into liquid state, vacuum suction can be applied removed the melted component. A centrifugal process may also be applied to remove the melted components.

A space 308 between mold components 210 and 310 defines a thin membrane 106 between upper chamber 102 and lower chamber 103. Mold components 210 and 310 are positioned relative to one another so that the thin membrane 106 is flexible. When pressurized air is pumped into upper chamber 102, upper chamber 102 expands by pushing thin membrane 106 downwards. If lower chamber 103 contains liquid, then the downward movement of thin membrane 106 will push the liquid out of the lower chamber 103. Multi-chamber microdevice 100 can be used as an air-driven liquid valve or a component of a peristaltic micropump.

The example shown in FIGS. 1–4 uses two elongated mold components 302a and 302b to support mold component 210. In an alternative example, only one elongated mold component 302a is used to support mold component 210. In the latter case, when multi-chamber microdevice 100 is cast, only one channel (e.g., 104a ) is connected to chamber 102.

Figure 5:
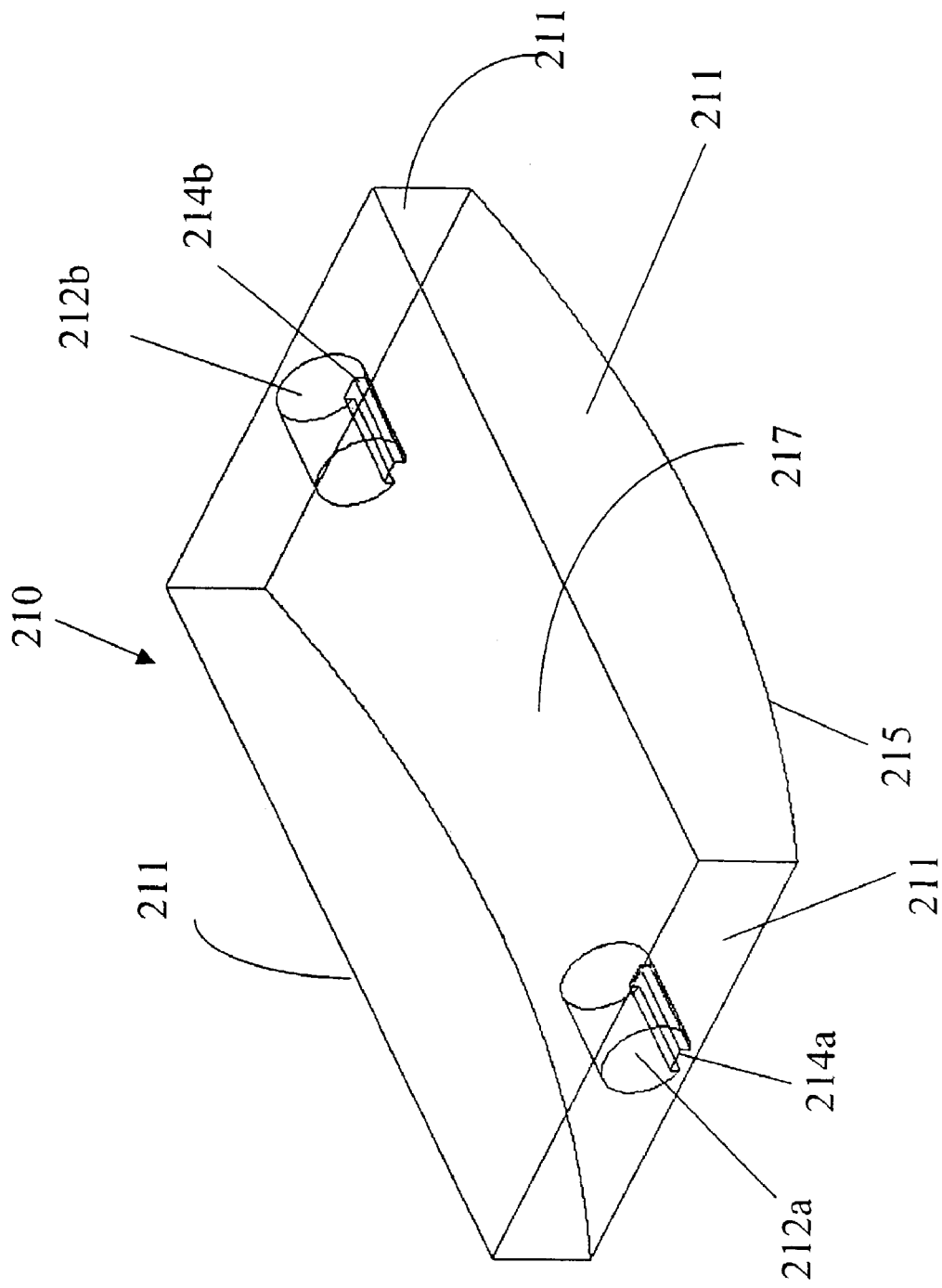
FIG. 5 shows a perspective view of a mold component used in the device mold.

Referring to FIG. 5, mold component 210 includes recess structures 212a and 212b for receiving the ends of mold components 302a and 302b, respectively. Ridge structures 214a (214b) prevents mold component 210 from moving relative to mold component 302a (302b).

Figure 6:
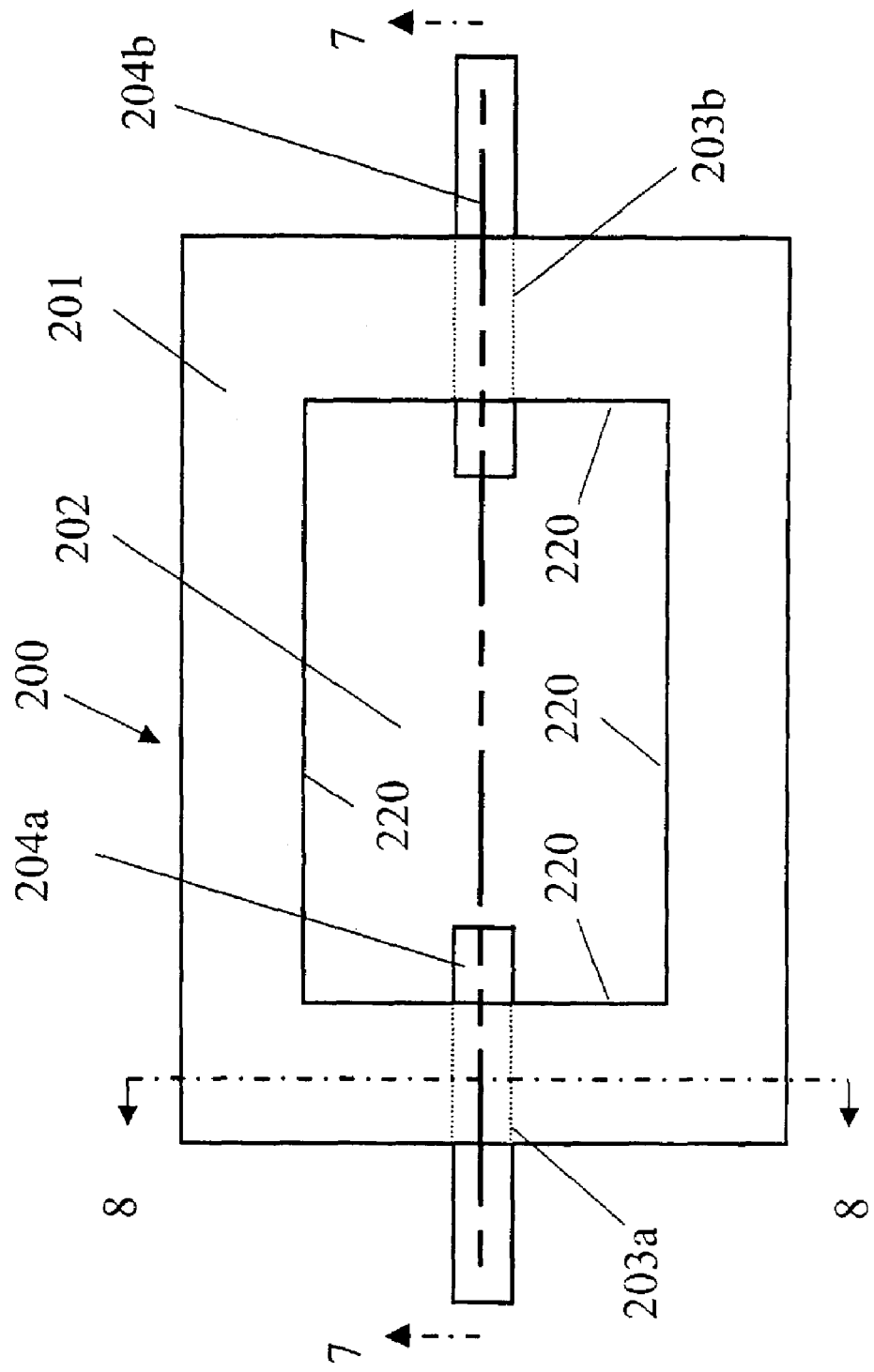
FIG. 6 shows top views of a component mold used to cast the mold component of FIG. 5.
Figure 7:
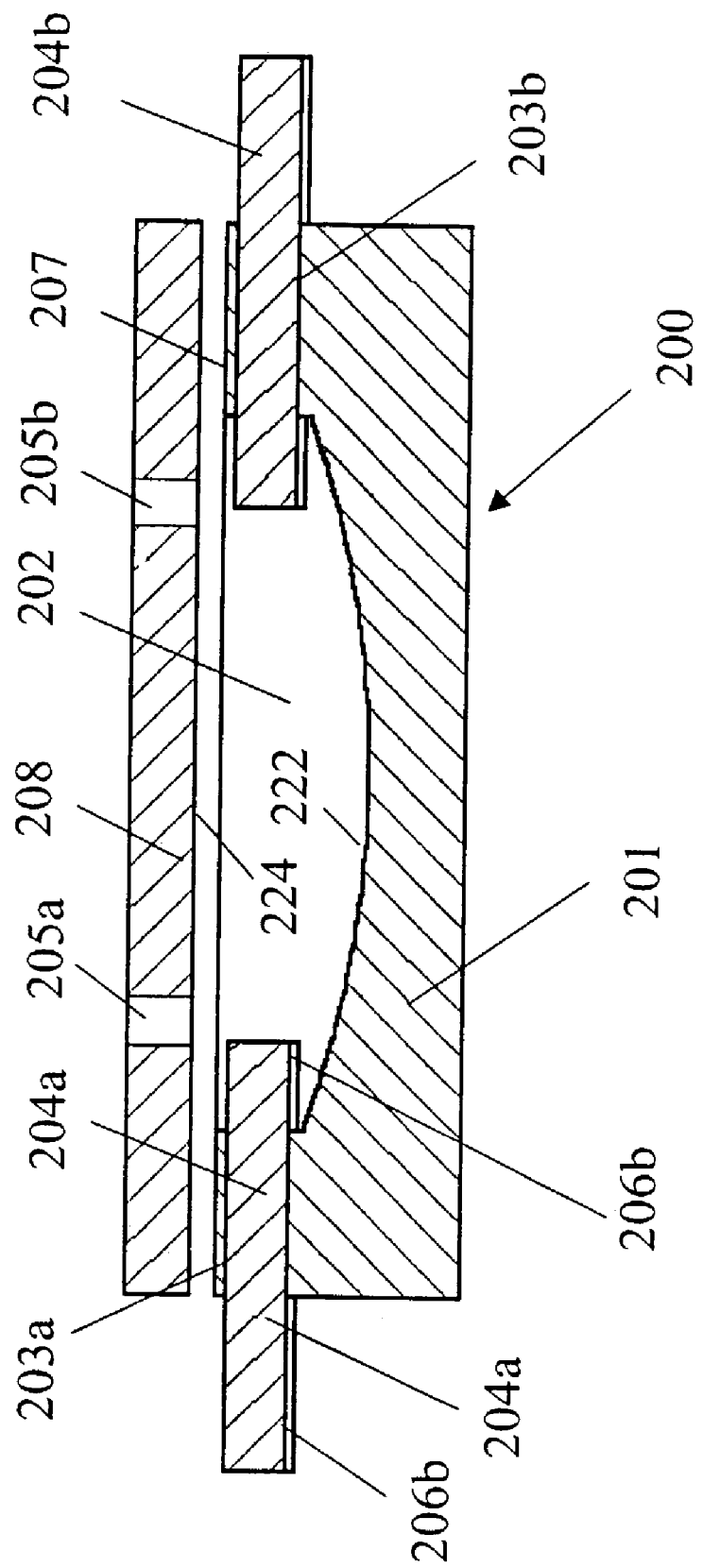
FIGS. 7 and 8 show cross sectional views of the component mold.
Figure 8:
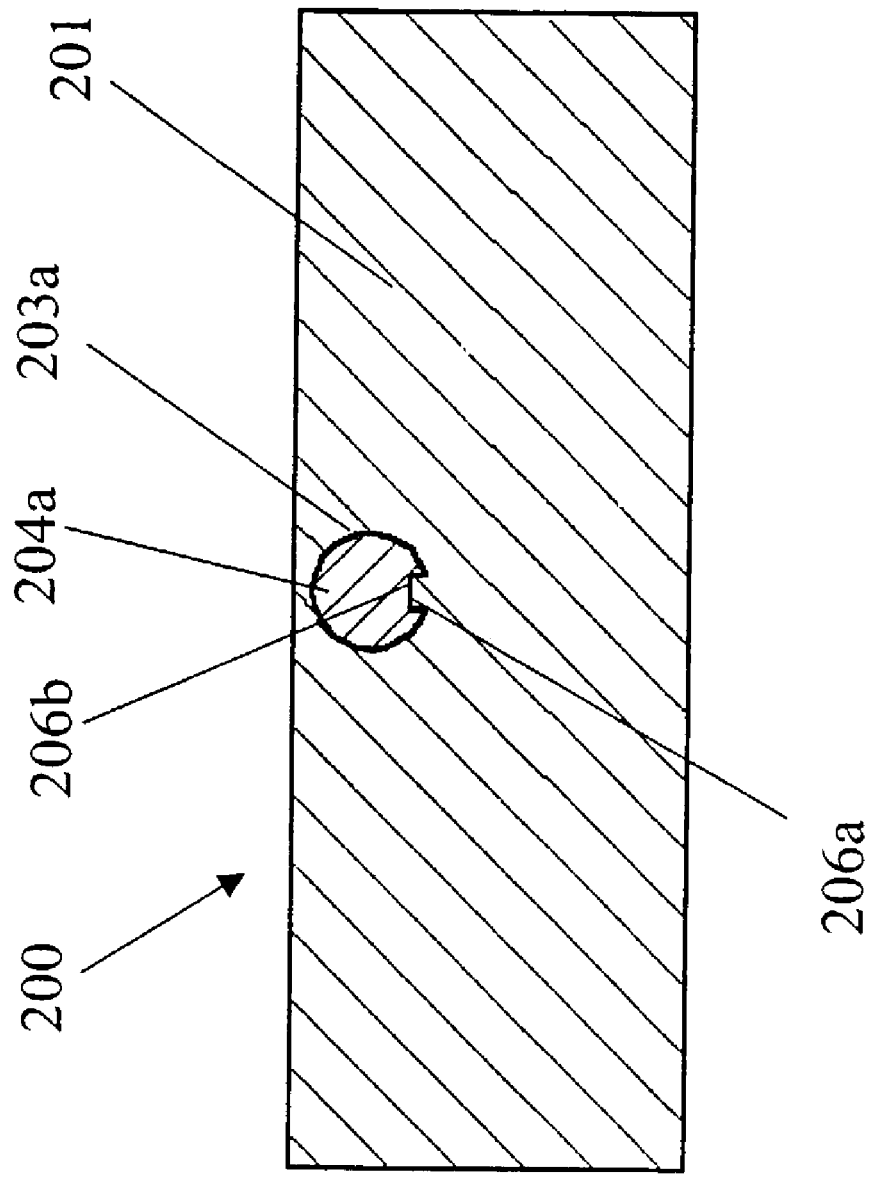

FIGS. 6–8 shows a process for fabricating mold component 210. FIG. 6 shows a top view of a component mold 200 that is used to cast mold component 210 (FIG. 5). FIG. 7 shows a cross section of component mold 200, where the cross section is along a plane 7 that is perpendicular to the plane of FIG. 6. FIG. 8 shows a cross section of component mold 200, where the cross section is along a plane 8 that is perpendicular to the plane of FIG. 6.

Referring to FIGS. 6–8, component mold 200 is formed by assembling a mold body 201, mold components 204a and 204b, and a mold cover 208. Mold components 204a and 204b have elongated shapes (e.g., like rods). Mold body 201 includes two holes 203a and 203b, that allows mold components 204a and 204b, respectively, to pass through. Mold body 201, mold cover 208, and mold components 204a and 204b in combination form an enclosed space 202 that defines the shape of mold component 210. Component mold 200 has an inner surface 222 that defines the shape of a bottom surface 215 of mold component 210 (FIG. 5). Inner surfaces 220 define the shape of side surfaces 211 of mold component 210. Inner surface 224 define the shape of a top surface 217 of mold component 210.

Mold body 201 has a ridge structure 206a protruding into hole 203a. Mold component 204a has an indent structure 206b that runs lengthwise of mold component 204a, and has a shape such that indent structure 206b fits snugly with ridge structure 206a so as to prevent mold component 204a from moving relative to the castable mold component 210. Similar structures are used to prevent mold component 204b from moving relative to mold body 201. The portion of indent structure 206b on mold component 204a that is exposed in space 202 defines the shape of the ridge structure 214a of the castable mold component 210. Similar structures on mold component 204b define the ridge structure 214b of the castable mold component 210. Mold body 201, mold cover 208, and mold components 204a and 204b can be made of steel, silicon, or plastic, and can be fabricated using, for example, microfabrication or sterolithography techniques.

Device mold 200 may have two openings, such as holes 205a and 205b on the mold cover 208 that connect space 202 to an exterior of device mold 200. When a reversible material is used to fabricate mold component 210, the reversible material can be heated into liquid state and poured or injected into the space 202 through the one of the openings. The temperature is lowered so that the reversible material solidifies into mold component 210. When a sublimable material is used to fabricate mold component 210, the sublimable material (in powder form) can be compressed into space 202 through one of the openings. Cover 208, mold components 204a and 204b are removed from mold component 210. Mold component 210 is released from mold body 201.

In an alternative example, where pour casting techniques are used, component mold 200 may have an open top, and cover 208 is not used. In yet another example, where die casting techniques are used, component mold 200 can be a two-piece structure (mold body 201 and cover 208).

Mold component 210 retains its dimensions after being cast from the component mold 200. Usually, there is little change in geometry of the mold component 210 as a result of the solidification. This means that the size of space 202 in component mold 200 can be made substantially the same as the desired size of upper chamber 102. If mold component 210 is made of a material such that the dimensions of mold component 210 changes (e.g., shrinks) after the material solidifies, component mold 200 may be designed so that the space 202 is slightly larger than the desired size of upper chamber 102 to compensate for the change in dimensions during solidification of the material. If mold component 210 is made of a reversible material, then after multi-chamber microdevice 100 is cast and mold component 210 is melted, the melted material may be reused to cast other mold components.

Figure 9:
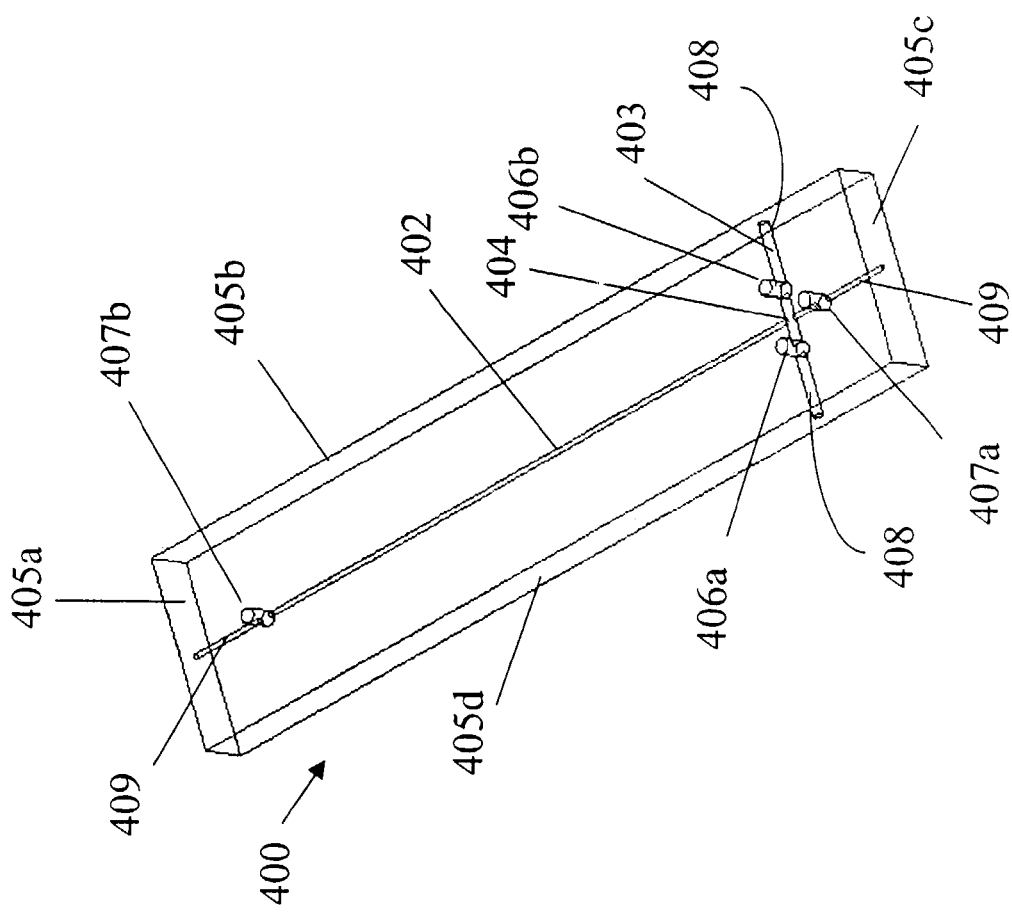
FIG. 9 shows a perspective view of a multi-channel microdevice.
Figure 10:
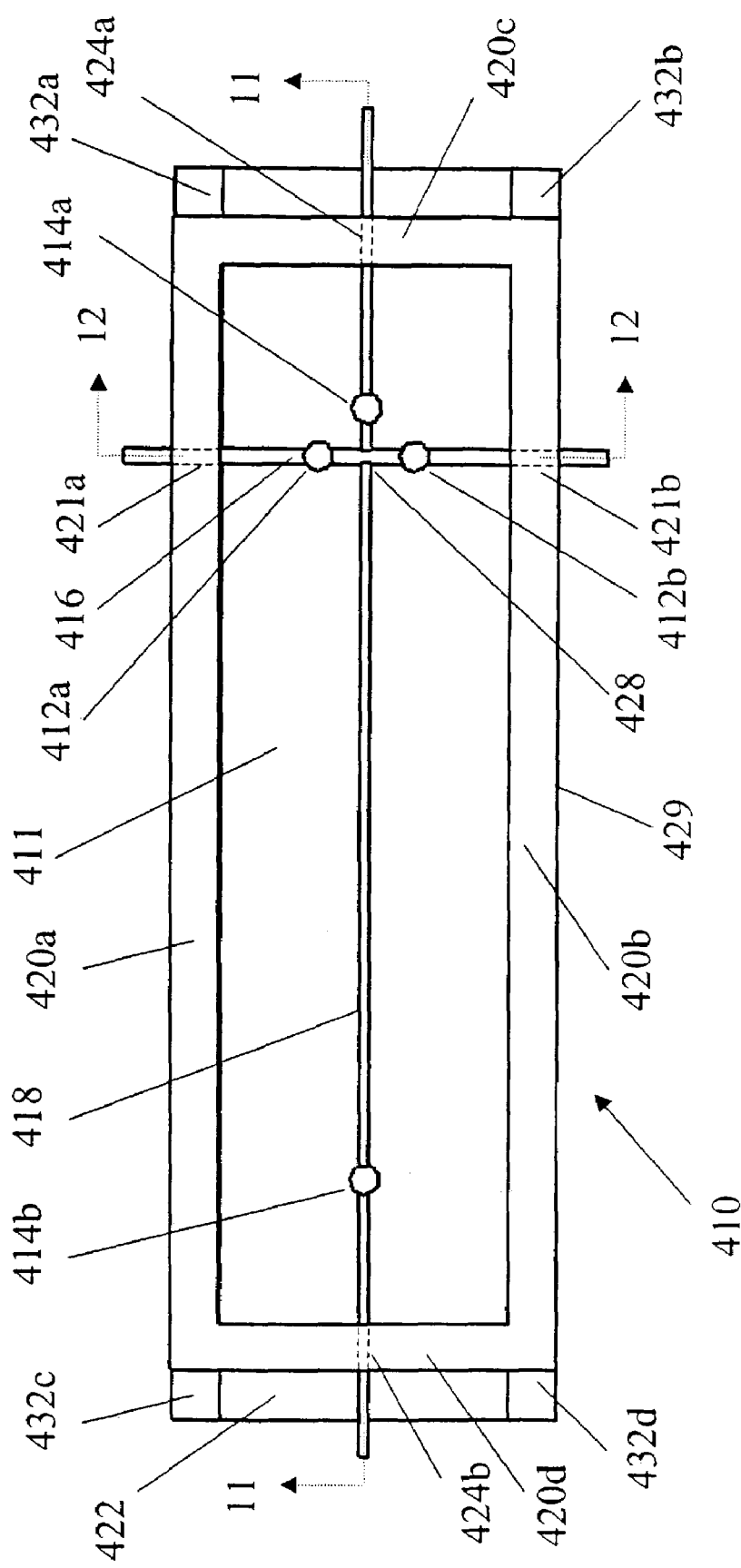
FIG. 10 shows a top view of a device mold used to cast the multi-channel microdevice of FIG. 9.
Figure 11:
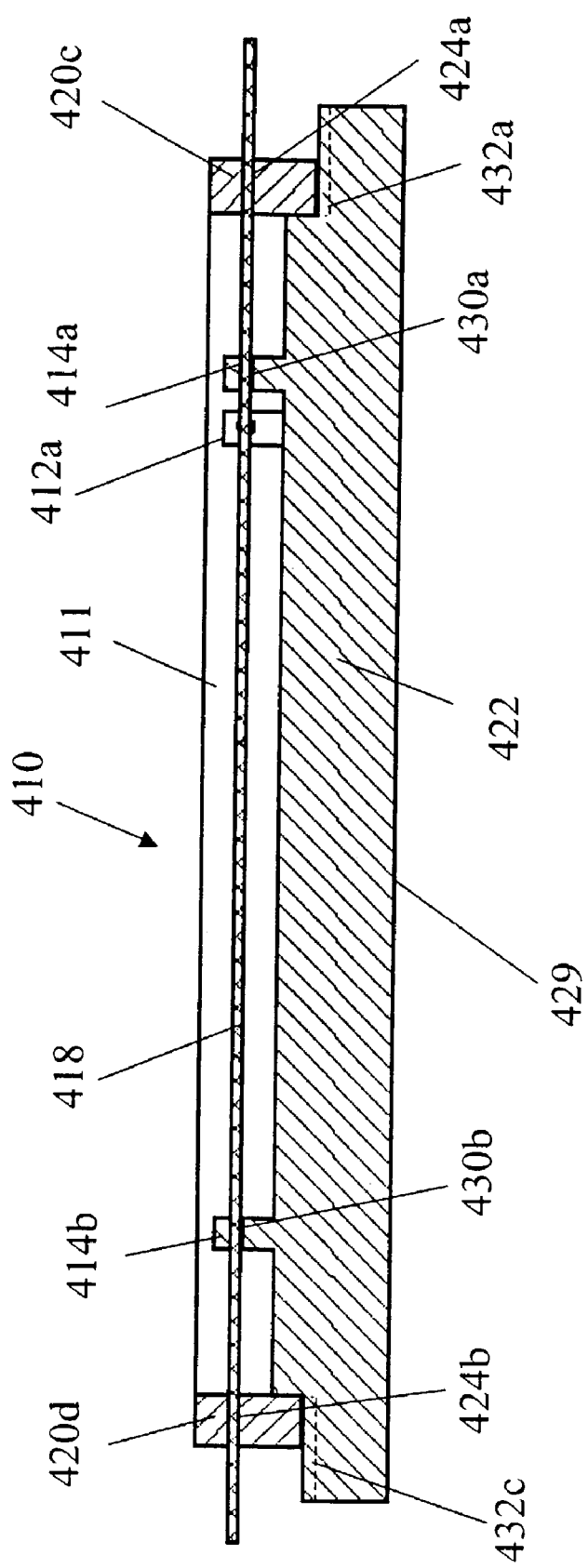
FIGS. 11–12 show cross sectional views of the device mold.
Figure 12:
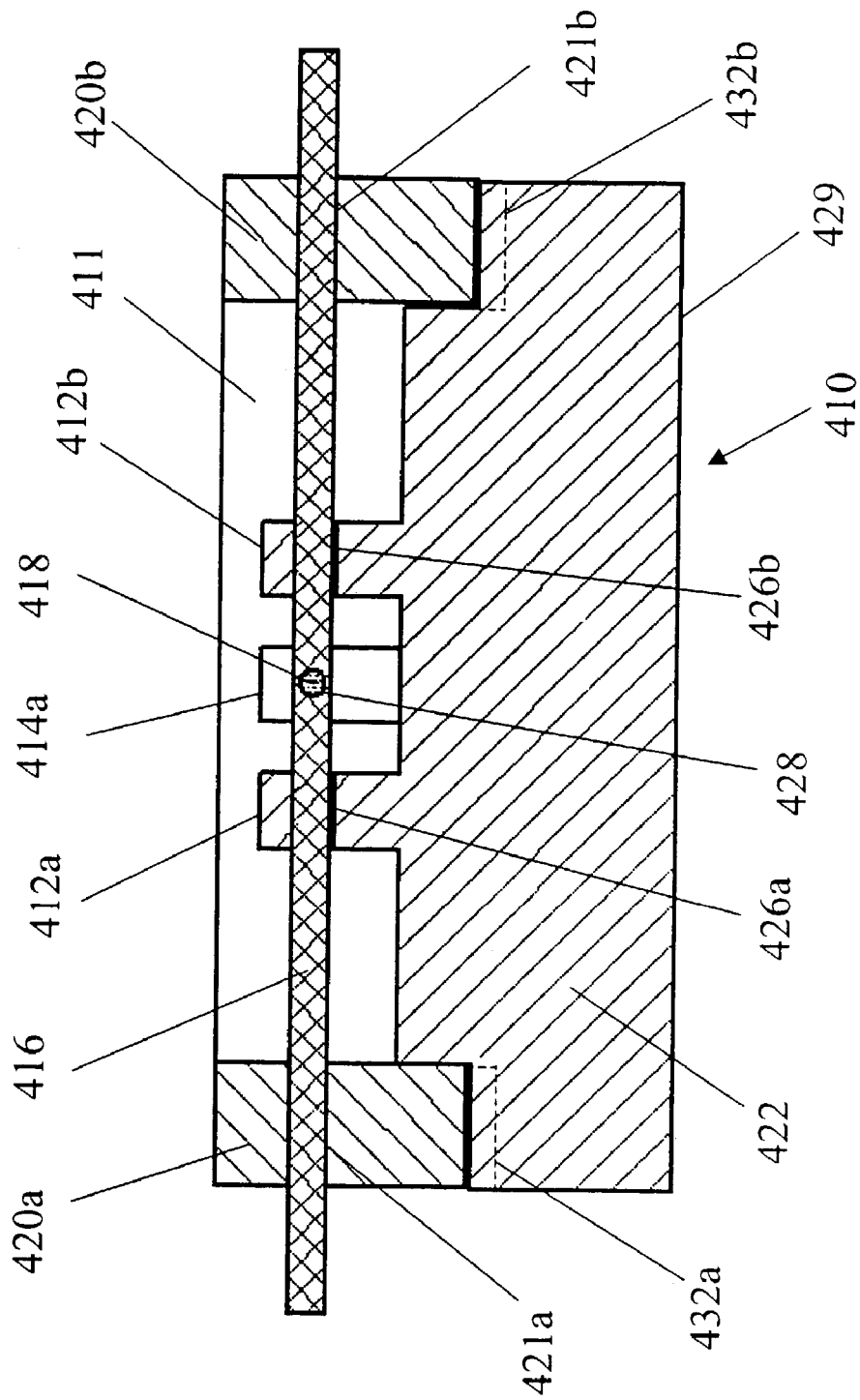

FIG. 9 shows a multi-channel microdevice 400. FIG. 10 shows a top view of a device mold 410 for casting the multi-channel microdevice 400. FIG. 11 shows a cross sectional view of device mold 410, where the cross section is along a plane 11 that is perpendicular to the plane of FIG. 10. FIG. 12 shows a cross sectional view of device mold 410, where the cross section is along a plane 12 that is perpendicular to the plane of FIG. 10.

Referring to FIG. 9, a multi-channel microdevice 400 includes a separation channel 402, an injection channel 403, and embedded reservoirs 406a, 406b, 407a, and 407b. The diameter of channel 403 is larger than the diameter of channel 402. Channels 402 and 403 intersect at an intersection 404. Multi-channel microdevice 400 can be used in electrophoresis. Electrodes can be connected to embedded reservoirs 406a, 406b, 407a, and 407b from their top openings. By applying voltages to the electrodes inserted into the reservoirs 406a and 406b, charged particles move from the reservoir 406a to the reservoir 406b. When a voltage difference is applied to electrodes inserted into reservoirs 407a and 407b, a plug of the particles at the intersection 404 moves toward the reservoir 407b. Particles with different charge or weight will move at different speeds along channel 402, and thus can be separated and analyzed.

Referring to FIGS. 10–12, device mold 410 is assembled from a mold body 429 and various mold components. Mold body 429 includes mold base 422 and sidewalls 420a–420d. Mold base 422 includes posts 412a, 412b, 414a, and 414b, which define the shapes of embedded reservoirs 406a, 406b, 407a, and 407b, respectively, in multi-channel microdevice 400. The mold components include wires 416 and 418, which define the shapes of injection channel 403 and separation channel 402, respectively.

Sidewalls 420a and 420b have holes 421a and 421b, respectively, that allow wire 416 to pass through. Sidewalls 420c and 420d have holes 424a and 424b, respectively, that allow wire 418 to pass through. Posts 412a and 412b have holes 426a and 426b, respectively, that allow the wire 416 to pass through. Posts 414a and 414b have holes 430a and 430b, respectively, that allow wire 418 to pass through. Wire 416 includes a hole 428 that allow wire 418 to pass through. Device mold 410 includes slots 432a–432d for mold releasing.

In one example, wire 416 has a diameter of 100 μm, and wire 418 has a diameter of 200 μm. This cause separation channel 402 to have a diameter of 100 μm, and injection channel 403 to have a diameter of 200 μm.

Device mold 410 is assembled by connecting sidewalls 420a–420d on the mold base 422, pulling wire 416 through holes 421a, 426a, 426b, and 421b, and pulling wire 418 through holes 424a, 430a, 428, 430b, and 424b.

After device mold 410 is assembled, a liquid polymer is poured into a region 411 defined by mold body 429 (including mold base 422 and sidewalls 420a–420d) and the mold components (including wires 416 and 418, and posts 412a, 412b, 414a, and 414b). The liquid polymer cures or solidifies in device mold 410. After the liquid polymer is cured, wire 418 is pulled out, leaving a space that becomes the separation channel 402. Wire 416 is pulled out, leaving a space that becomes the injection channel 403. The fabricated multi-channel microdevice 400 is released from device mold 410 and turned over with the openings of embedded reservoirs 406a, 406b, 407a, and 407b on the top.

Portions 408 of channel 403 that extend from reservoirs 406a and 406b to sidewalls 405d and 405b, respectively, of microdevice 400 can be used to deliver fluid into channels 403 and 402, or be sealed by glue. Likewise, portions 409 of channel 402 that extend from reservoirs 407a and 407b to sidewalls 405c and 405b, respectively, of microdevice 400 can be used to deliver fluid into channel 402 and 403, or be sealed by glue For example, wires 416 and 418 can be steel wires, glass fibers, carbon fibers, or aramid fibers. Wires 416 and 418 can be straight or have constant curvatures so that the wires can be pulled out of device mold 410. The diameters of the wires 416 and 418 are selected to be substantially the same as the desired diameters of channels 403 and 402, respectively. The diameters of wires 416 and 418 can range from nanometers to micrometers, depending upon the application. Reversible, sublimable, and soluble materials can also be used to create wires 416 and 418.

The techniques for fabricating multi-chamber microdevice 100 and multi-channel microdevice 400 can be used to fabricate microstructures in a microfluidic device. Other microdevices, such as microsensors, may also be fabricated using similar techniques. Medical microdevices can also be achieved in biomedical applications. Such microdevices can include implantable microsystem for medical diagnostics or drug delivery.

Figure 13:
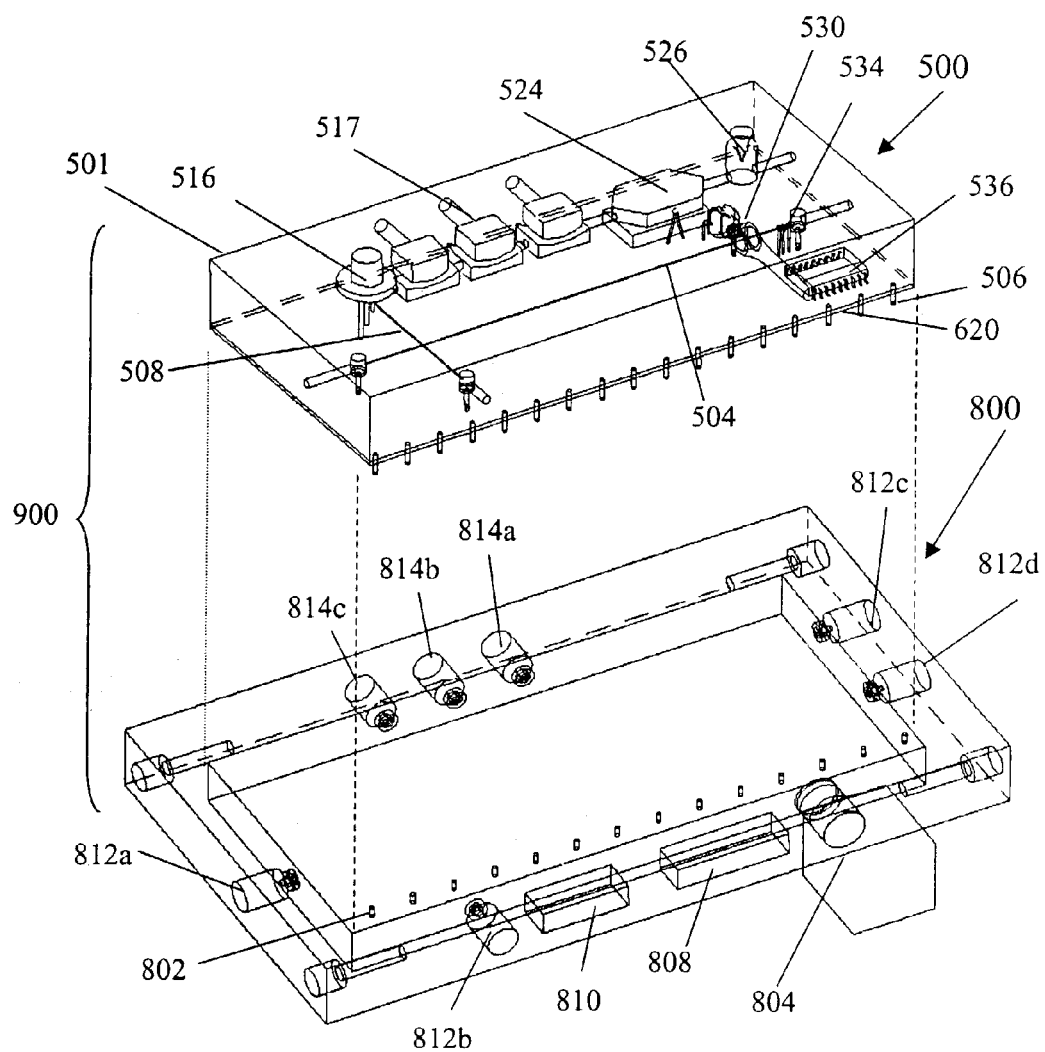
FIG. 13 shows an exploded view of a microfluidic system.
Figure 14:
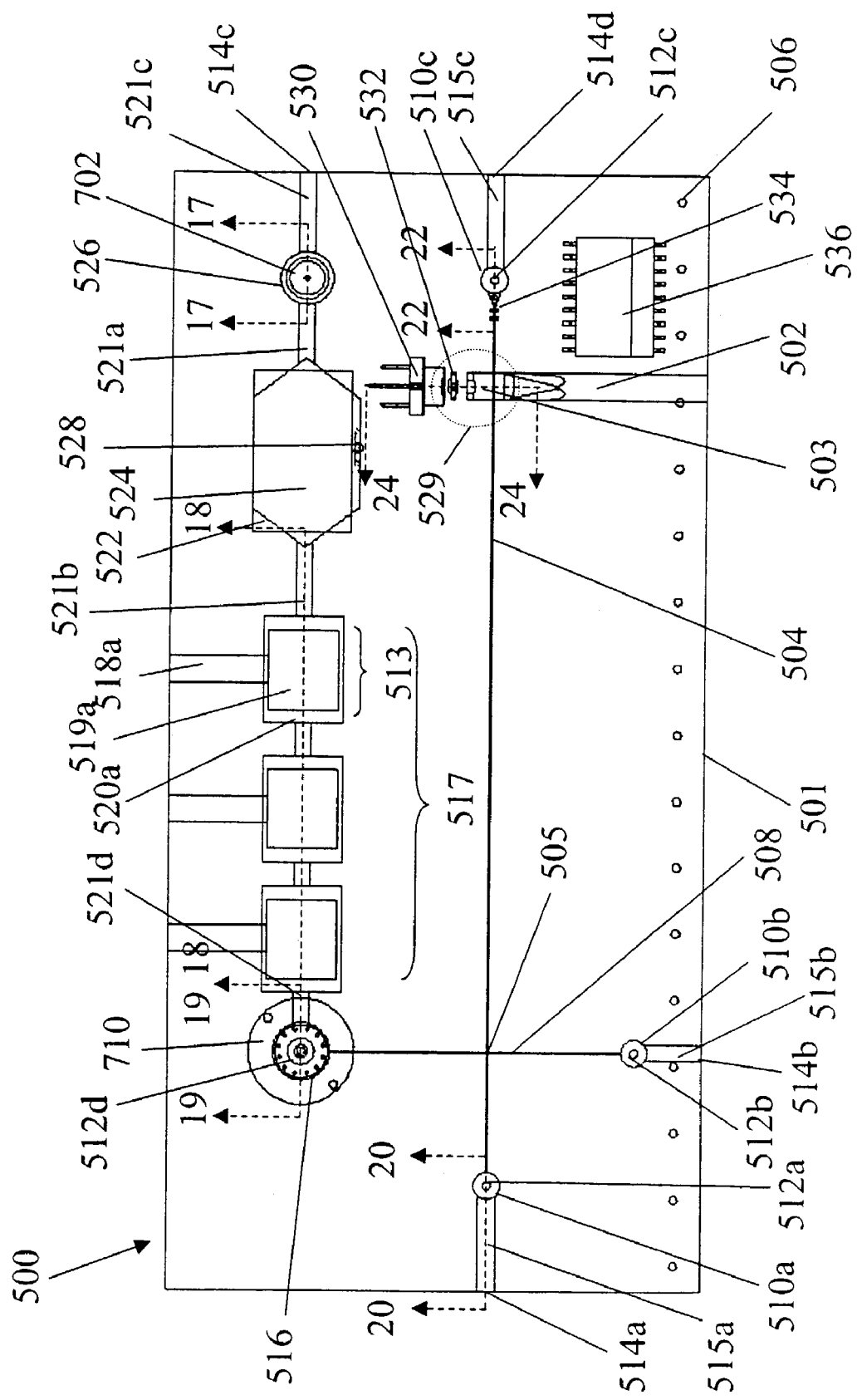
FIG. 14 shows a top view of the microfluidic device.
Figure 15:
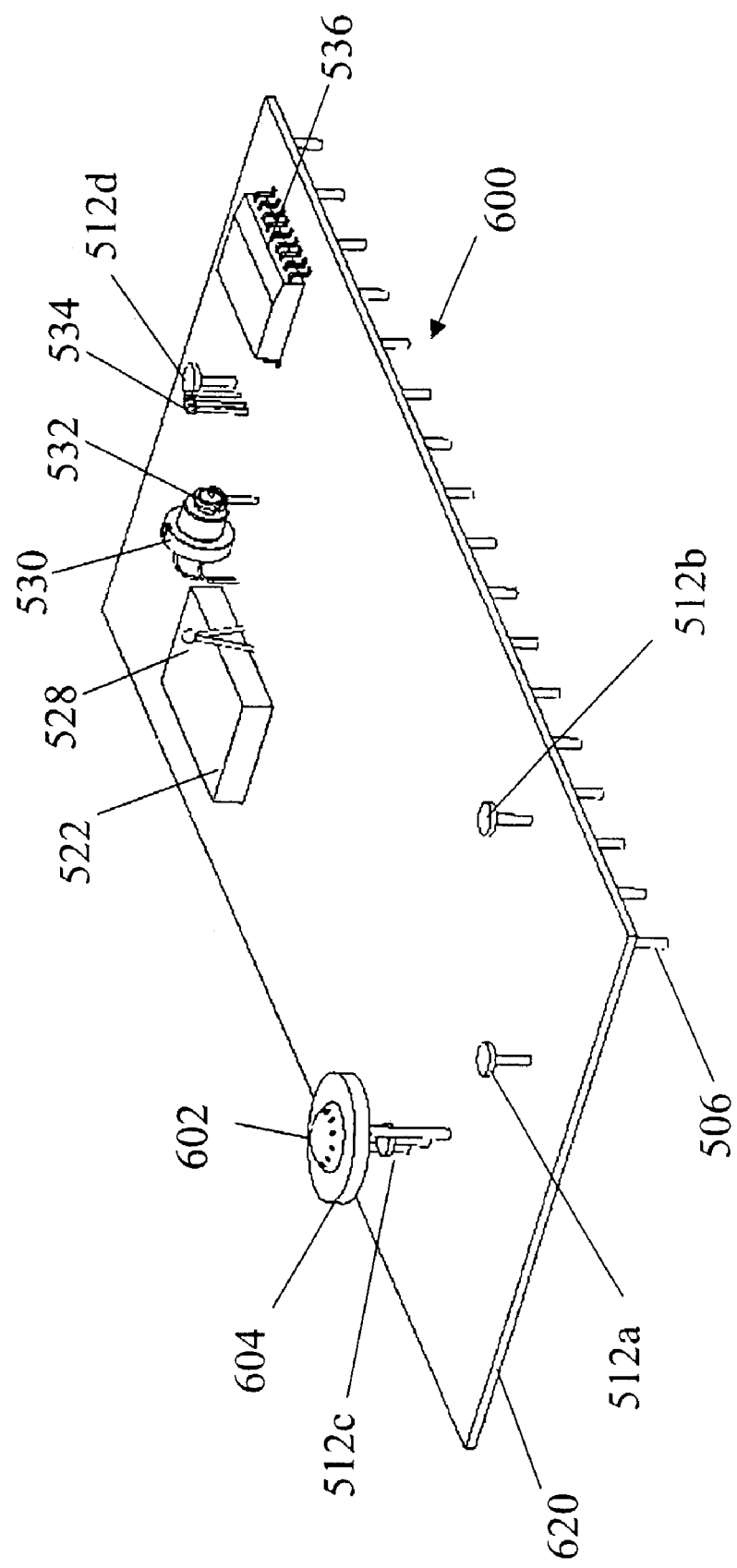
FIG. 15 shows a platform that includes a circuit board and function components.

Referring to FIGS. 13–15, an integrated microfluidic system 900 that may be used in DNA analysis includes a microfluidic device 500, and a cassette 800. Microfluidic device 500 includes a microdevice body 501 having predefined structures that form microfluidic components and an integrated platform 600 having functional components mounted thereon. To fabricate microdevice body 501, a device mold is constructed by assembling a mold body, platform 600, and various mold components. Some or all of the mold components can be made of reversible, sublimable, or soluble materials.

Microdevice body 501 is cast from the device mold by pouring liquid polymer into the device mold and curing the liquid polymer so that it solidifies. Techniques for removing mold components from device molds 300 and 410 can be used to remove the mold components from the device mold for fabricating microdevice body 501. The microfluidic device 500 is then released from the mold body. In one example, platform 600 includes an integrated circuit board 620 having functional components soldered to the circuit board 620.

Microfluidic device 500 includes fluidic parts, such as a sample loading reservoir 526 (FIG. 17), a polymerase chain reaction (PCR) chamber 524, a peristaltic micropump 517 (FIG. 18), chambers for a microvalve 516 (FIG. 19), a separation channel 504, an injection channel 508, fluidic interfaces 514a–514d, and a pneumatic interface 518a (FIG. 14).

Microfluidic device 500 includes detection and controlling parts, such as circuit board 620, a laser diode 530, a microlens 532, an integrated circuit 536, a microheater 522, a thermal sensor 528, electrodes 512a–512d, an electrode set 534, a ring microheater 604, a domed diaphragm 602 made of shape memory alloy, and connection pins 506. Thermal sensor 528 is integrated inside PCR chamber 524, and microheater 522 is placed beneath PCR chamber 524. Connection pins 506 provides electrical interfaces for various electronic components, such as laser diode 530, microheater 522, thermo sensor 528, electrode set 534, microheater 604, and electrodes 512a–512d. Light waveguides 502 and 503 (FIG. 24) for fluorescence emission detection is also integrated inside the microdevice body 501.

Cassette 800 (FIGS. 13 and 25) includes a bottom wall 801a and sidewalls 801b. The bottom wall 801a has electrical sockets 802 for interfacing the connection pins 506 in the microfluidic device 500. The sidewalls 801b have pneumatic interfaces 814a–814c for interfacing micropump 517, fluidic interfaces 812a–812d for supplying liquid to the interfaces 514a–514d on the sides of microfluidic device 500, electrical interfaces 808 and 810 for interfacing electrical components connected to electrical sockets 802, and a photo sensor 804 for detecting light signals.

The following describes a process for conducting DNA analysis using microfluidic system 900.

A running buffer is loaded from the fluidic interface 514c into the microfluidic device 500 filling all the chambers and channels. A sample containing DNA fragments is injected by a pipette into sample loading reservoir 526. The pump 517 operates to pump the sample from sample loading reservoir 526 to PCR chamber 524 through a channel 521a. The sample in PCR chamber is thermocycled by microheater 522, and the temperature of the sample is measured by microsensor 528. Microheater 522 and microsensor 528 are connected to integrated circuit 536, which controls the microheater 522 to adjust the temperature of PCR chamber to facilitate the multiplication of DNA segments. Then the sample is pumped to a chamber 710 of a microvalve 516 using peristaltic micropump 517. Micropump 517 includes three sub-pumps 513. Each sub-pump 513 includes a pneumatic interface (e.g., 518a), an air chamber (e.g., 519a), and a liquid chamber (e.g., 520a). The pneumatic interfaces 518a–518c are connected to pneumatic interfaces 814a–814c on the cassette 800 and then to a source that supplies pressurized air (not shown).

Figure 19:
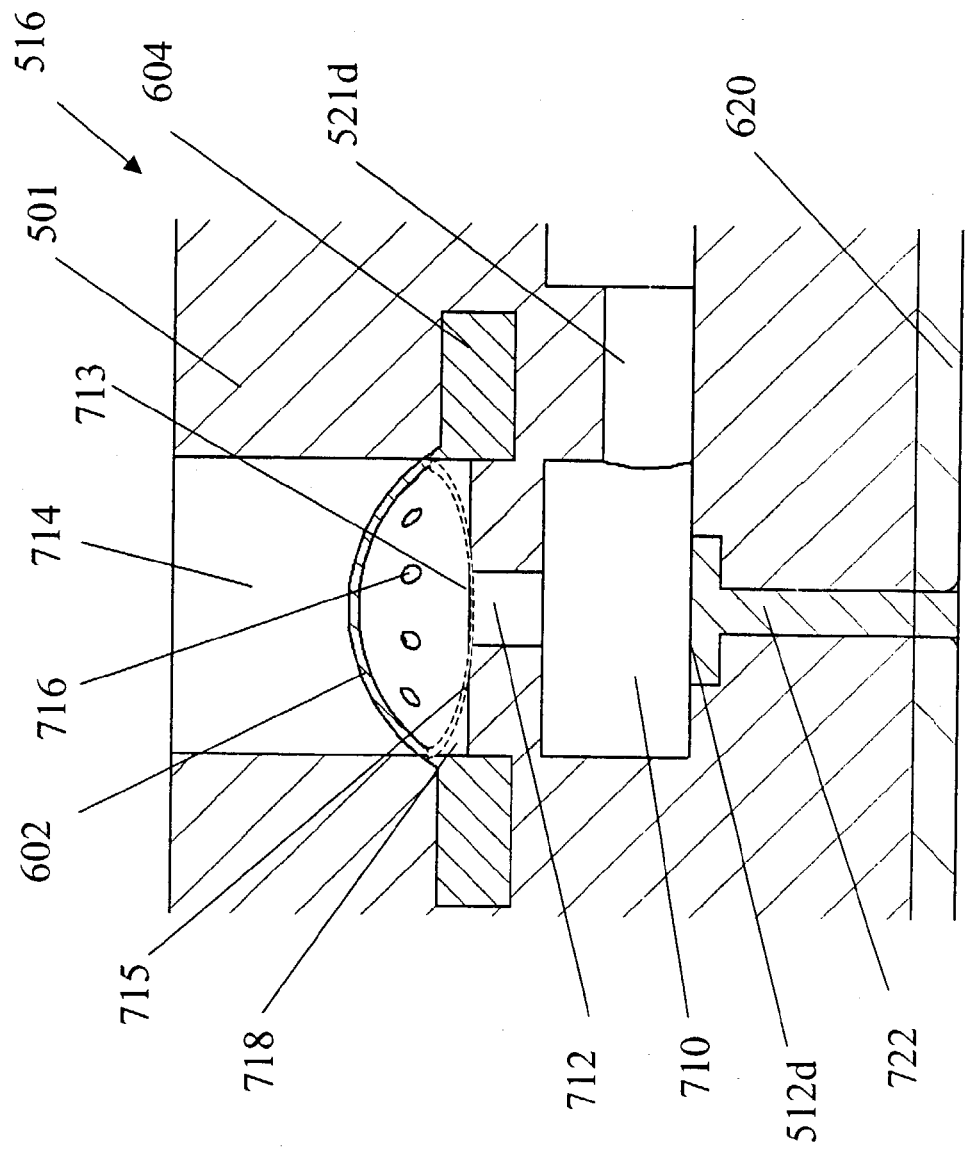
FIG. 19 shows a cross sectional view of a microvalve.

Detail of microvalve 516 is shown in FIG. 19. The chamber 710 is connected to an embedded reservoir 510b through an injection channel 508. An embedded reservoir 510a is connected to another embedded reservoir 510c through a separation channel 504. Injection channel 508 and separation channel 504 are connected at an intersection 505. Electrodes 512a–512d are integrated with embedded reservoirs 510a–510c band chamber 710, respectively. Applying a voltage (e.g., 300 V) across electrodes 512d and 512b generates an electro-osmotic (or electrophoretic) flow that causes the sample in chamber 710 to flow through injection channel 508 towards embedded chamber 510b. Applying a voltage (e.g., 1000 V) across electrodes 512a and 512c generates an electro-osmotic (or electrophoretic) flow that causes a plug of the sample at the intersection 505 to flow from intersection 505 towards embedded reservoir 510c, thereby separating the DNA fragments in the fluid along the length of separation channel 504 according to their weight and charge.

The DNA fragments are detected by a technique called capillary electrophoresis, in which laser-induced fluorescence detection is used. As the fluid containing DNA fragments flow through a detection region 529 of separation channel 504, the DNA fragments are illuminated by a laser beam emitted from diode laser 530. A microlens 532 focuses the laser beam onto detection region 529. In an alternative setup, an external laser can be used with a mirror or a waveguide integrated inside microfluidic system 900 at the position of the laser diode 530 to deliver the laser beam from the external laser to detection region 529. The DNA fragments are bonded with fluorescent tags, which produce fluorescence emission when excited by the laser beam.

An O-shaped optical waveguide conduit 503 directs emission scattered from the DNA fragments towards an optical waveguide 502, which guides the fluorescence emission to the photo sensor 804 in the cassette 800. By analyzing the signals detected by photo sensor 804, it is possible to determine the type of fluorescent tags passing through detection region 529, hence determining the type of DNA fragments in the fluid. Capillary electrophoresis performed by using system 900 allows rapid, high-resolution, and high sensitivity detection of the DNA fragments.

The DNA fragments can also be detected using a technique called electrochemical detection, which can monitor small volumes of the DNA fragments separated inside separation channel 504. A set of electrochemical electrodes 534 reacts with DNA fragments that pass through a detection region 535 of separation channel 504. During the reaction, electrons are gained or lost at the electrode, which generates electrical signals that can be processed by integrated circuit 536.

The set of electrochemical electrodes 534 includes three electrodes (FIG. 22): a working electrode 756, a reference electrode 754, and a counter electrode 752. Electrodes 754 and 756 are embedded in microdevice body 501, and have tips that are ring-shaped (FIG. 23). The ring-shaped tips have inner diameters the same as the diameter of the channel 504. The surface of the ring-shaped tips of electrodes 754 and 756 form part of the surface of channel 504. Channel 504 is connected to a cone-shaped chamber 750, which is connected to embedded reservoir 510c. Electrode 752 is a tip electrode that extends into cone chamber 750 and contacts the fluid flowing in cone chamber 750. The set of electrochemical electrodes 534 are mounted on circuit board 620 and connected to integrated circuit 536, which amplifies and processes signals detected by the set of electrodes 534.

In one example, segments (e.g., 515a–515c) of channels from the reservoirs to the sidewalls of the microdevice body 501 can be used as interfaces to connect channels 504 and 508 to an exterior of microfluidic device 500. The segments 515a–515c of channels can be used for injecting or removing liquid from channels 504 and 508, such as when cleaning channels 504 and 508. In another example, the segments 515a–515c of channels can be used to couple microfluidic device 500 to other systems, such as the cassette 800. In yet another example, the segments 515a–515c of channels may be sealed after the microdevice body 501 is released from the mold body.

FIG. 15 shows a perspective view of integrated platform 600. The platform 600 includes a circuit board 620, on which electrical and optical components are mounted.

Figure 16:
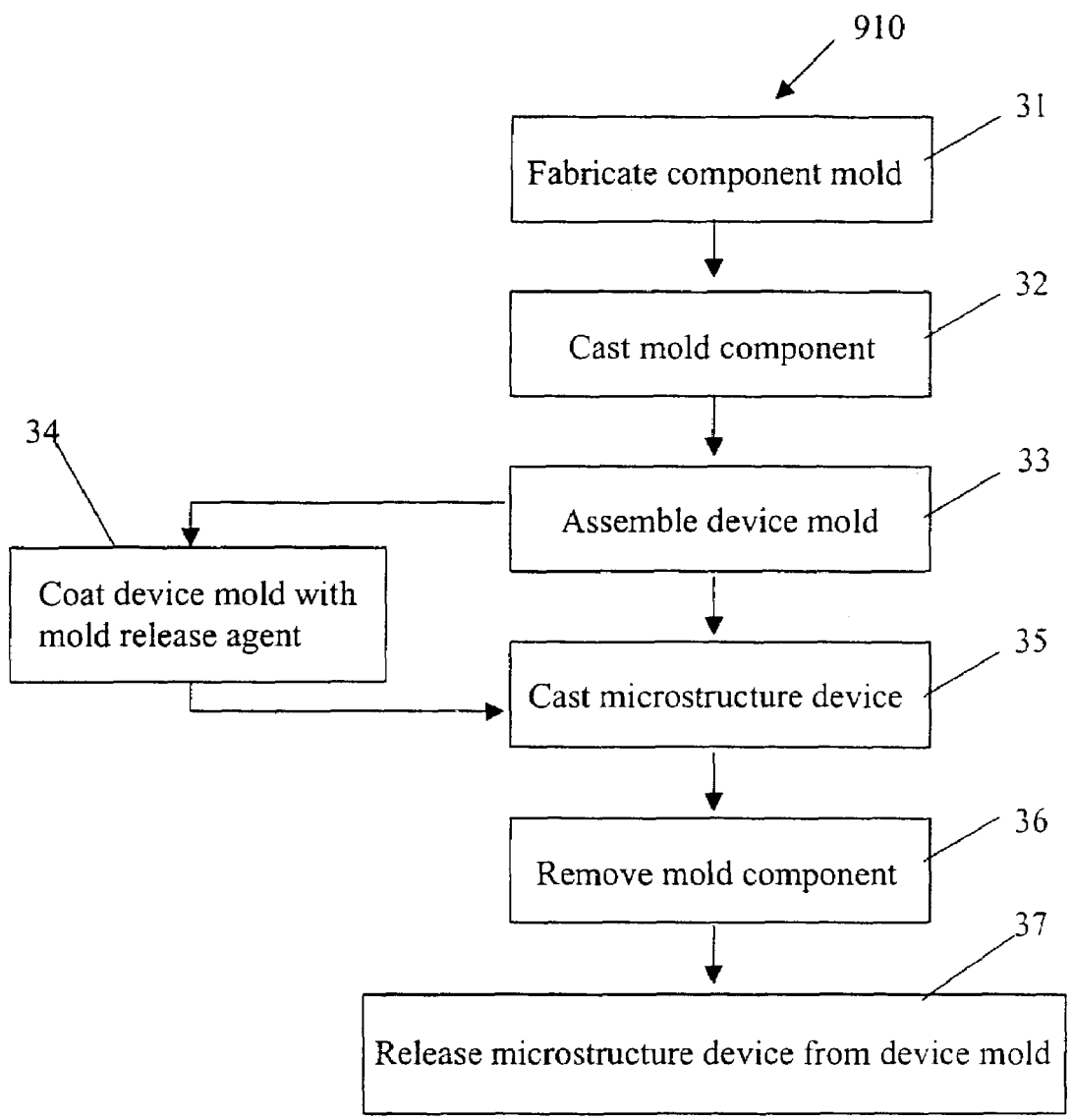
FIG. 16 shows a process for fabricating microstructures in the microfluidic device.

Referring to FIG. 16, a process 910 is used to fabricate microstructures inside a solid body by using micro-mold components to define the microstructures. Process 910 includes the following steps:

Step 31: Fabricating component molds. Component mold 200 is fabricated to cast mold components 210, which are used to define the air chambers 519a–519c of micropump 517. Another component mold is fabricated to cast mold components 310, which are used to define the liquid chambers 520 of micropump 517. Similarly, other component molds are fabricated or assembled to cast additional mold components that are used to define additional microstructures in microdevice body 501.

Step 32: Casting mold components. Reversible, sublimable, or soluble materials are poured, injected, or compressed into the component molds fabricated or assembled in step 31. After the material solidifies, the mold components are separated from the component molds.

Step 33: Fabricating and assembling the device mold. A device mold for casting microdevice body 501 is assembled using a mold body, various mold components, and the integrated platform 600. For example, mold components 210 and 310 may be used to define the shapes of chambers 519a and 520a, respectively, of micropump 517. Wires 416 and 418 may be used to define the shapes of injection channel 508 and separation channel 504, respectively. A mold component 742 (FIG. 21) may be used to define the shapes of embedded reservoirs 510a–510c. The device mold can be open on the-top for pour casting, or be a closed structure for injection casting.

Step 34: Coating the surfaces of the mold device, including the mold body and mold components, with a mold release agent. This step may be omitted when liquid polymer is used for casting the microdevice body and the microdevice body does not adhere to the mold body and mold components.

Step 35: Casting the microstructure body. Liquid polymer is poured or injected into the device mold to fill in the space defined by the mold body and the mold components. The liquid polymer is selected so that its melting temperature is lower than the melting (or sublimation) temperature of the mold components.

Step 36: Removing the mold components from the microstructure body 501. Where mold components (e.g., 210 and 310) are supported by rods (e.g., 302a–302d), these rods are melted or pulled away from the device mold. Removing the rods create channels in the microdevice body 501. These channels provide access for removing the mold components (e.g., 210 and 310) from the microdevice body 501. The mold components may be heated so that they melt (or vaporize), or a solvent may be used to dissolve the mold components. The melted or dissolved mold components are removed by use of vacuum suction force or centrifugal force.

Step 37: Releasing the microdevice body 501 from the mold body.

An advantage of using microfluidic system 900 is to eliminate off-line sample processing. This is accomplished by integration of sample and reagent handling, reaction, and detection within a single microfluidic system 900. Microfluidic system 900 allows electrophoretic analysis, including fluidic handling, polymerase chain reaction, laser-induced-fluorescence detection, and electrochemical detection to be performed on a single integrated device.

In the example of microfluidic system 900, there are eight functional parts that are integrated: (1) the sample loading reservoir 526; (2) the PCR chamber 524, the microheater 522, and thermal sensor 528; (3) the three-stage peristaltic micropump 517; (4) the microvalve 516; (5) the microchannels 504 and 508 for separation analysis; (6) the electrodes 510a–d for voltage application; (7) the LIF detection by laser diode 530, microlens 532, waveguides 503 and 502, optical filter 806, and photo sensor 804; (8) the electrochemical detection by electrode set 534 and its appropriate electronics 536.

Figure 17:
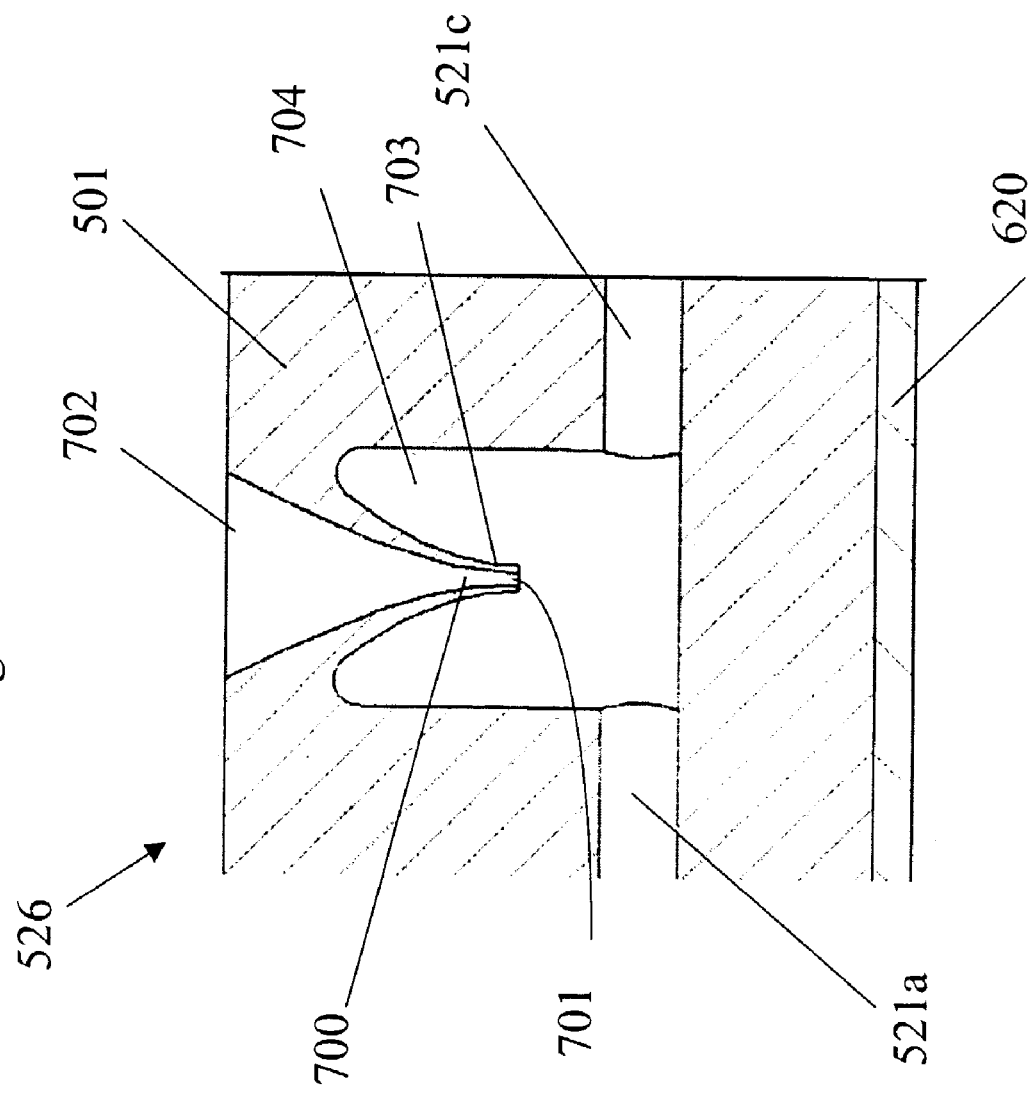
FIG. 17 shows a sample loading reservoir.
Figure 18:
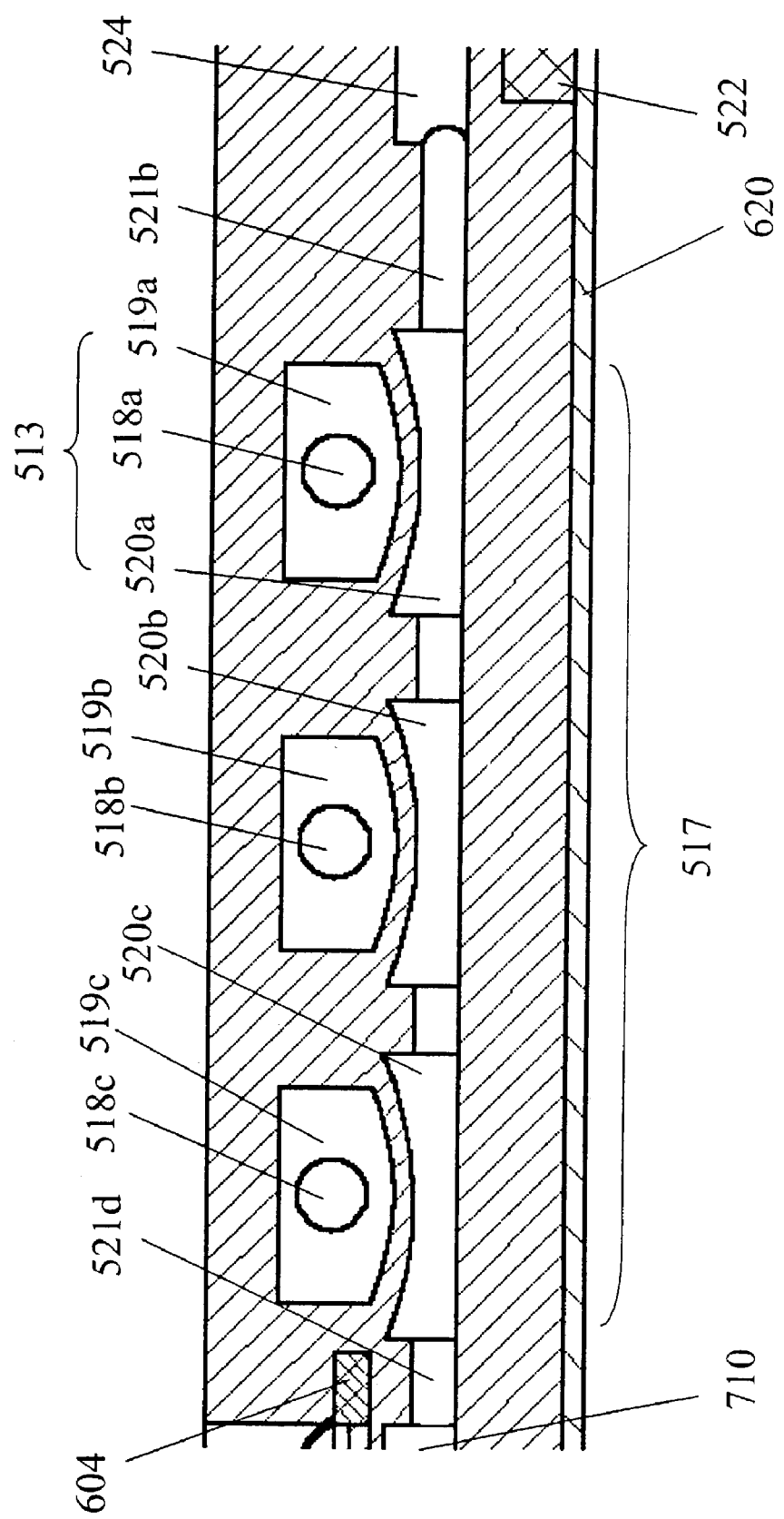
FIG. 18 shows a cross sectional view of a peristaltic micropump.

Referring to FIG. 17, sample loading reservoir 526 includes a fluidic chamber 704, an inlet channel 521c, an outlet channel 521a, and a V-shape funnel 702 connected to fluidic chamber 704 through a funnel tip 700. Outlet channel 521a connects to the PCR chamber 524 (FIG. 18). When loading a sample, a tip of a pipette having the sample is pushed through the V-shape funnel 702 and funnel tip 700. After the sample is transferred from the pipette to fluidic chamber 704, the sample is pumped to the PCR chamber 524 (FIG. 18) through channel 521a.

When flushing the channels and the chambers using a liquid, the liquid flows from inlet channel 521c into chamber 704 and to outlet channel 521a. Funnel tip 700 is designed to have a thin flexible wall 703 and a small opening 701. Opening 701 opens when a pipette tip is pushed through funnel tip 700 in a direction from V-shape funnel 702 to chamber 704. When liquid is flushed into chamber 704 from inlet channel 521c, the pressure of the flushing liquid squeeze the thin wall 703 of the funnel tip 700 so that opening 701 is closed. This prevents the flushing liquid from flowing out through the funnel 702.

PCR chamber 524, and air chambers 519a–519c, and liquid chambers 520a–520c of the micropump 517 can be created by mold components that are similar to mold component 210 depicted in FIG. 5. An elongated mold component, such as a small wire or a rod, can be used to pass through and string together the mold components for the PCR chamber 524 and micropump 517. After microdevice body 501 is cast and cured, the elongated members, such as the wires, rods, or sheets, are pulled out to create channels, such as 521a–521d, that connects the chamber 704 of sample loading reservoir 526, PCR chamber 524, micropump 517, and microvalve 516. Three elongated mold components, such as rods or sticks, support the three mold components for defining the three air chambers 519a–519c. After microdevice body 501 is cast and cured, the elongated members are pulled out to create pneumatic interfaces 518a–518c.

Referring to FIG. 18, peristaltic micropump 517 is operated using four-stage cycles: Stage 1 (519a-D, 519b-D, 519c-I)→stage 2 (519a-I, 519b-D, 519c-D)→stage 3 (519a-I, 519c-D)→stage 4 (519a-D, 519b-I, 519c-I), where D means deflated, and I means inflated.

Referring to FIG. 19, microvalve 516 is actuated by using a domed diaphragm 602 made by shape memory alloy (SMA) surrounded by a ring microheater 604. Domed diaphragm 602 has small holes 716. Electrical connections (not shown) connect ring microheater 604 to printed circuit board (PCB) 620. Microvalve 516 includes a lower chamber 710 that connects a channel 521d from chamber 520c of micropump 517. Microvalve includes an upper chamber 718, an interconnecting channel 712, and a top vent 714.

At the bottom of chamber 710, there is an electrode plate 512d, connected to a lead 722, which is soldered to the PCB 620. Electrode plate 512d is used to apply a voltage to the fluid in chamber 710.

Microvalve 516 operates in two states: an open state and a closed state. To operate microvalve 516 in the closed state, electric current is applied to ring microheater 604 to heat diaphragm 602. This causes diaphragm 602 to curve downwards, as shown in dished line 715, such that a center portion 713 of diaphragm 602 seals the channel 712 connecting upper chamber 718 to lower chamber 710. To operate microvalve 516 in the open state, the electric current is not applied to ring microheater 604, causing diaphragm 602 to cool and to restore to its normal shape, which has a shape that curves upwards, as shown in solid lines. This allows fluid or air to flow freely from lower chamber 710 to upper chamber 718 through interconnecting channel 712, and from upper chamber 718 to top vent 714 through holes 716.

Microvalve 516 is typically operated in its open state when a sample is pumped from the sample loading reservoir 526 to PCR chamber 524 and from PCR chamber 524 to lower chamber 710. Microvalve 516 is typically operated in its closed state for buffer loading or channel flushing when liquid is pumped from fluidic interface 514c to PCR chamber 524, liquid chambers 520a–520c, lower chamber 710, then to injection channel 508 and separation channel 504. The buffer fluid or flushing fluid is pumped out of microfluidic device 500 through fluidic interfaces 514a, 514b, and 514d.

Microvalve 516, with its SMA domed diaphragm 602 and ring microheater 604, shows an example of mechanical integration within a microfluidic device 500. Microvalve 516 can be replaced by a pressure-air-driven close-and-open structure having an upper chamber and a lower chamber, similar to chambers 519a and 520a of micropump 517, with a thin membrane 106 in between the upper and lower chambers. The microvalve is closed when pressured air is supplied to the upper chamber 519a, causing the thin film to flex downward to close interconnecting channel 712. The microvalve is opened when the pressured air is released from the upper channel, causing the thin film to return to its normal position, opening interconnecting channel 712.

Figure 20:
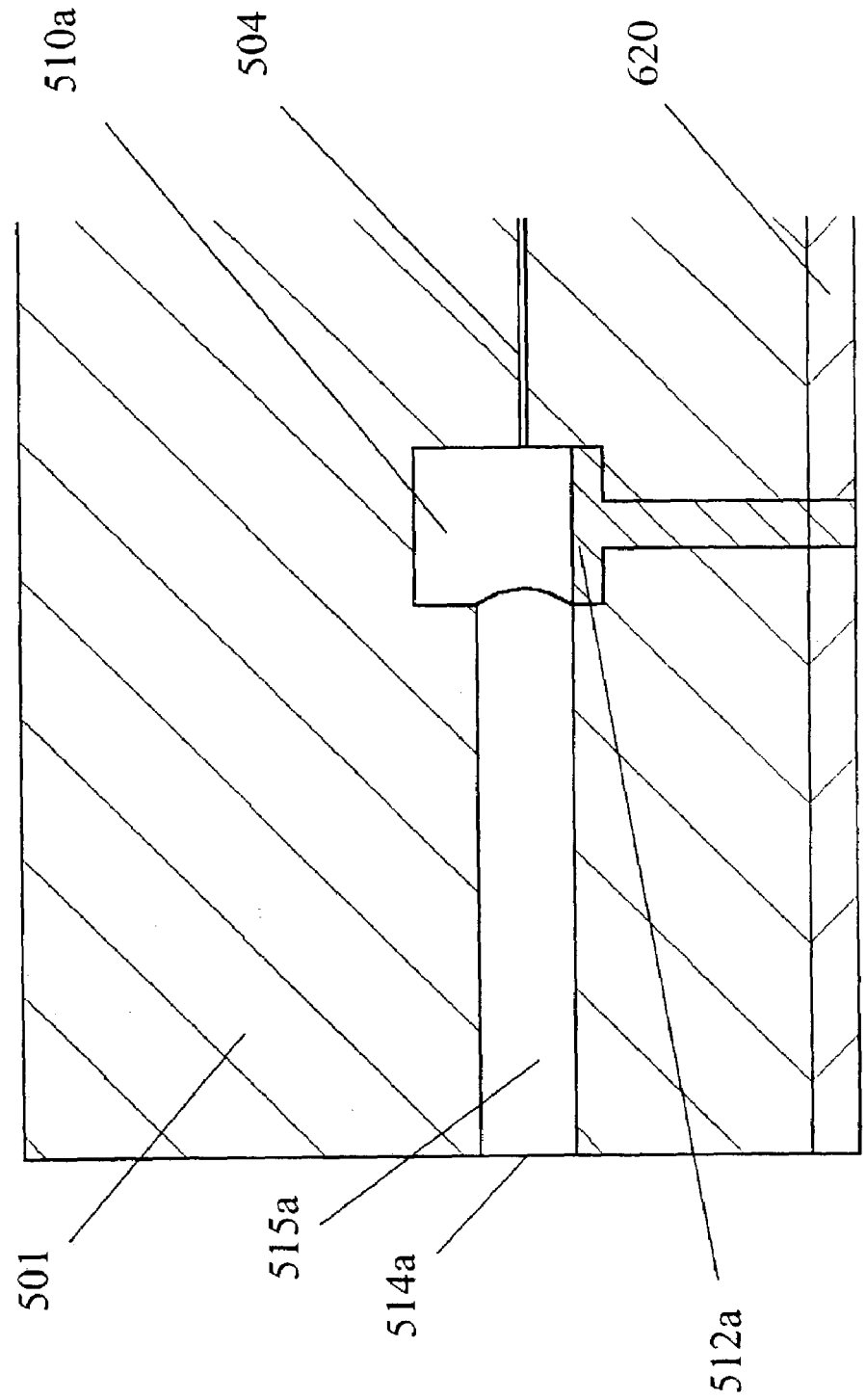
FIG. 20 shows a cross sectional view of an embedded reservoir integrated with an electrode and two channels.

Referring to FIG. 20, an embedded reservoir 510a is integrated with electrode 512a. Similarly, embedded reservoirs 510b and 510c are integrated with electrodes 512b and 512c, respectively. Electrode 512d is integrated with chamber 710 of microvalve 516. The electrodes are positioned below embedded reservoirs 510a–510c and chamber 710.

Because channels 504 and 508 have small diameters, it may be difficult to remove melted or dissolved mold components from channels having the same diameters as channels 504 or 508. Thus, an enlarged channel 515a is created to connect reservoir 510a to fluidic interface 514a at a sidewall of microdevice body 501.

Figure 21:
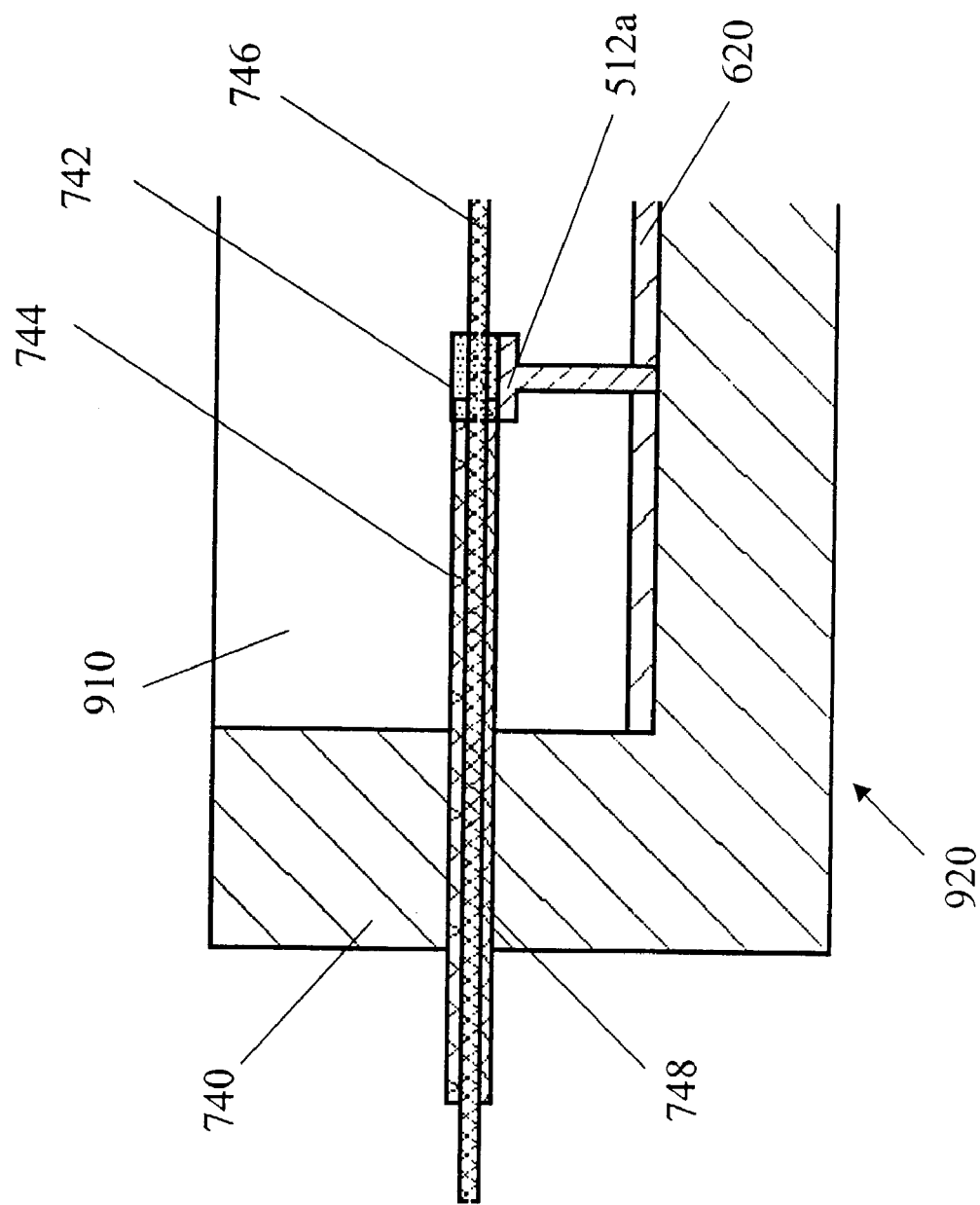
FIG. 21 shows a portion of a device mold used to fabrication the microstructure of FIG. 20.

Referring to FIG. 21, to create the structure shown in FIG. 20, a device mold 920 is assembled by connecting a mold component 742, electrode 512a, a part of printed circuit board 620, a wire 746, a solid tubing 744, and a mold body 740. Mold component 742 has a shape that is the same as a shape of embedded reservoir 510a. Solid tubing 744 has an inner diameter that is the same as a diameter of wire 746. Solid tubing 744 and wire 746 are pulled through a hole 748 on mold body 740. Wire 746 is threaded through tubing 744, and strings together mold component 742 and other mold components. Tubing 744 is partly inserted into mold component 742. After casting the microdevice body 501, wire 746 is pulled out from body 501 through tubing 744, creating channel 504. Tubing 744 is pulled out of hole 748, creating channel 515a, which has a diameter larger than channel 504. Having made channel 515a, mold component 742 can be easily removed from the microdevice body 501 to create chamber 510a.

Figure 22:
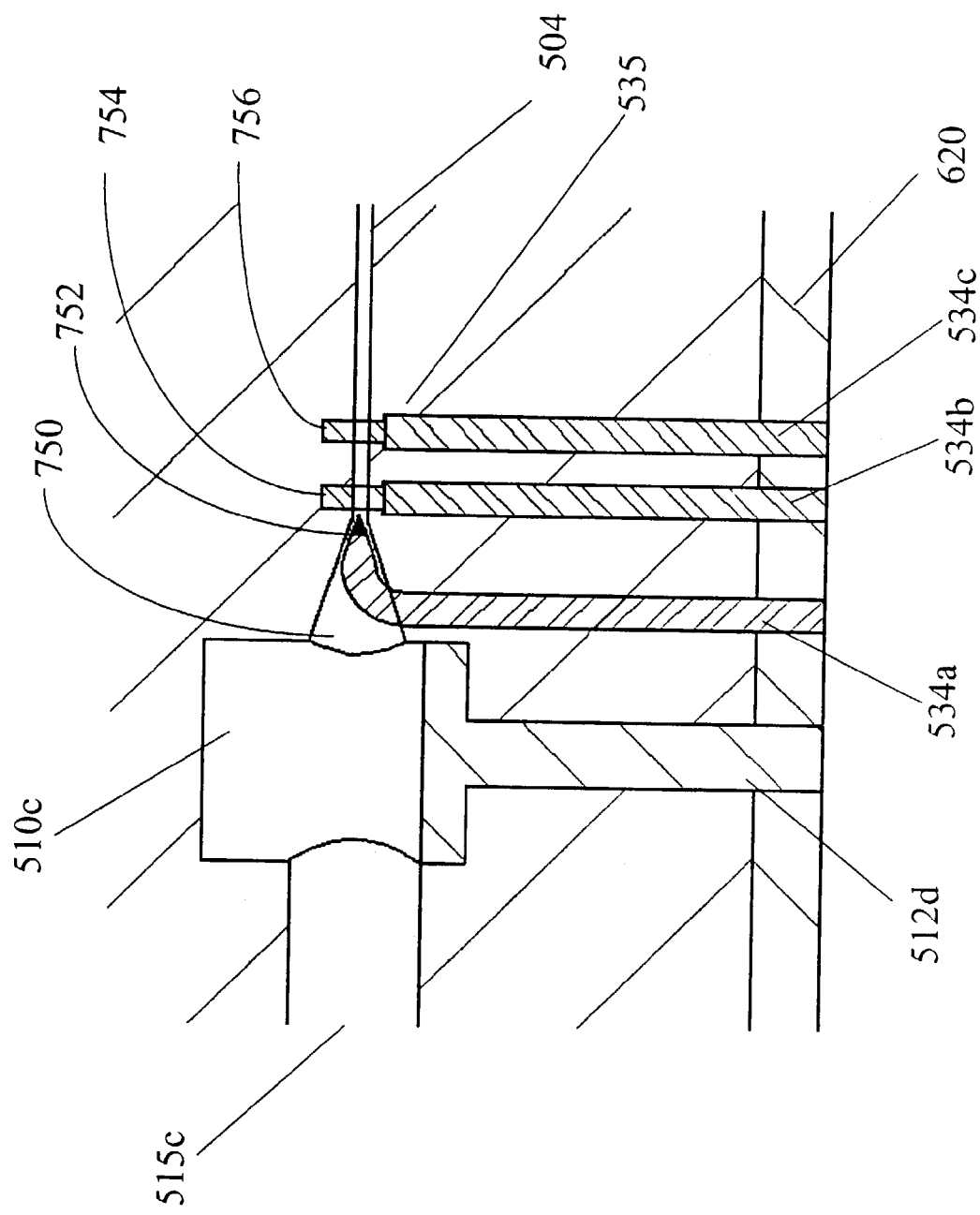
FIG. 22 shows electrodes used for electrochemical detection.
Figure 23:
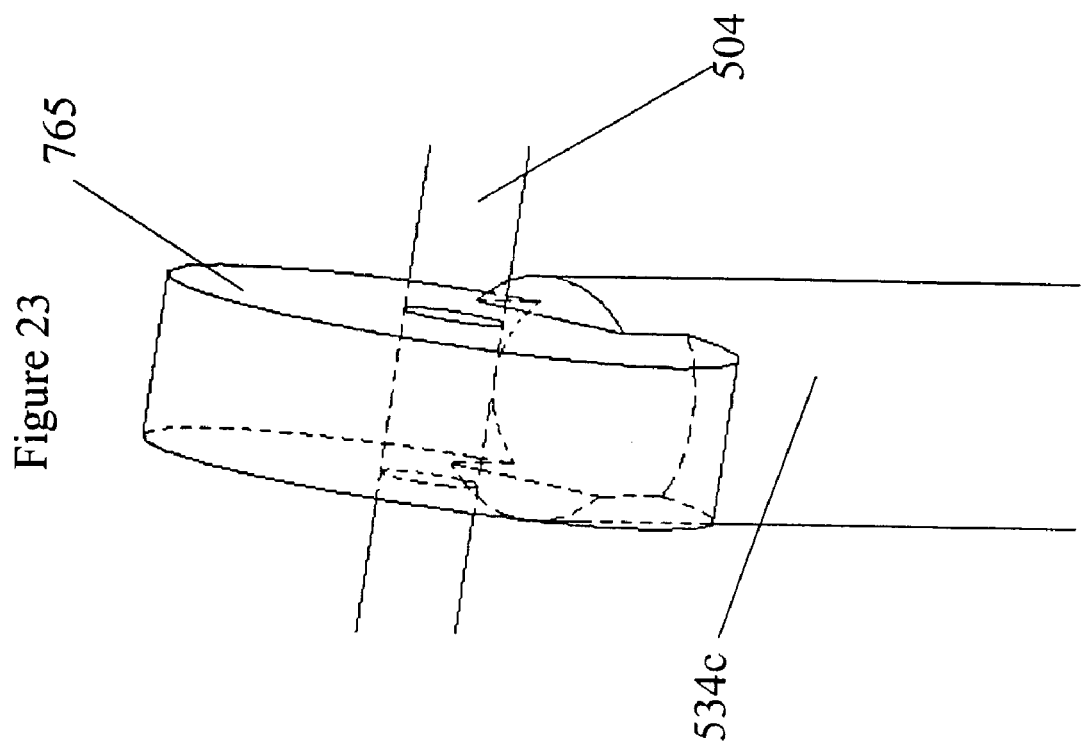
FIG. 23 shows an electrode.

Referring to FIGS. 22 and 23, an electrode set 534 includes two in-channel ring electrodes 754 and 756, and an end-channel electrode 752. The electrode set 534 is used to perform electrochemical detection at the end of the separation channel 504. Electrode set 534 includes a working electrode 756, a reference electrode 754, and a counter electrode 752. Electrodes 756 and 754 are ring shaped and surround separation channel 504. Portions of electrodes 756 and 754 contact the fluid flowing in channel 504. FIG. 23 shows a more detailed view of electrode 756 with the channel 504. These two electrodes 754 and 756 create an electrical signal that is dependent on chemical constituents of the fluid in channel 504 during separation analysis. Counter electrode 752 has a pointed tip electrode that extends into a cone chamber 750 that connects chamber 510c and channel 504. Leads 534a, 534b, and 534c serve as posts that connect electrodes 752, 754, and 756, respectively, to PCB 620 and to integrated circuit 536 for signal amplification and processing.

The following describes a processing for integrating electrodes 752–756 with microdevice body 501. Electrodes 752–756 and their leads 534a–534c are assembled on PCB 620 and positioned so that the center holes of the ring electrodes 754 and 756 and the tip of the electrode 762 are at the same level as the microchannel 504. A wire 746 is pulled through the center holes of the ring shaped electrodes 754 and 756. The tip of the wire is inserted into a cone shaped mold component that is used to create the cone shape chamber 750 and reservoir 510c. Electrode 752 is wedged inside the cone shaped mold component. After casting microdevice body 501, wire 746 is pulled out, and the mold components are removed from microdevice device 501. Electrodes 752, 754, and 756 become embedded inside the microdevice device 501 at proper positions suitable for electrochemical detection.

Figure 24:
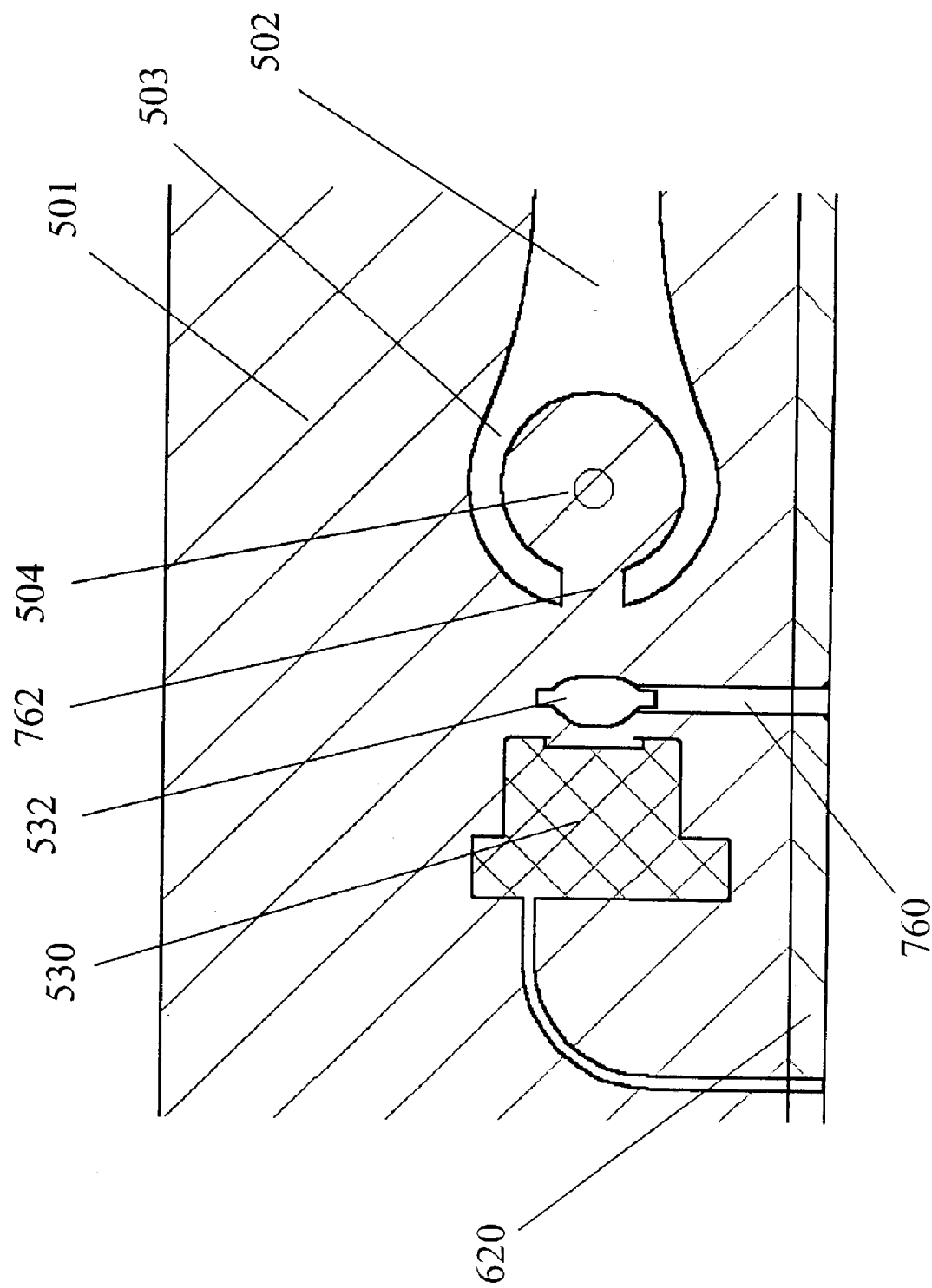
FIG. 24 shows microstructures for laser induced fluorescence detection.

Referring to FIG. 24, light induced fluorescence detection is performed by using laser diode 530, microlens 532, O-shape optical waveguide 503, and optical waveguide 502. Microlens 532 is supported by a holder 760. Laser diode 530 generates a laser beam to excite molecules labeled with fluorescent tags in the sample. To gather fluorescence emission, the O-shape optical waveguide 503 is designed to surround channel 504. Microlens 532 focuses the laser beam into the channel 504 through a small opening 762 on the O-shape waveguide 503. If the intensity or the wavelength of the laser diode 530 is not suited for the excitation, a mirror can be integrated at the position of the laser diode 530 to bend the external laser beam from the underneath of the microfluidic device 500. The laser beam can also be directly focused on channel 504 with an external focus lens positioned below channel 504. In the latter example, the hole 762 can be made at the bottom of the O-shape optical waveguide 503. A hole having a size approximately the same as hole 762 is also created on the circuit board 620 to allow the laser beam to pass through.

Optical waveguides 502 and 503 gather and deliver light from channel 504 to the photo sensor 804. Using the microfabrication techniques described herein, an optical waveguide can be integrated into a microdevice by creating a conduit with a certain shape and filling it with an appropriate liquid. The liquid has a refractive index greater than that of the microdevice material. Waveguide 502 transmits the fluorescent emission to an optical filter 806 then to a photo sensor 804 (FIG. 25). The inside wall of the waveguide conduit 502 and 503 may be coated with a material, such as Teflon AF resin, whose refractive index is less than a transparent liquid that is filled into the conduit. In this way, a liquid core waveguide can be created.

FIG. 25 shows a top view of cassette 800 that can be coupled to microfluidic device 500. Cassette 800 includes three adapters 814a–814c positioned on a sidewall 801. Adapters 814a–814c correspond to the pneumatic interfaces 518a–518c of micropump 517. Fluidic adapters 812a–812d (which are built on sidewalls of cassette 800) correspond to fluidic interfaces 514a–514d, respectively, of microfluidic device 500. Each adapter has an o-ring groove (e.g., 816) for fitting an O-ring seal to prevent leakage of pressurized air or liquid.

Electrical sockets 802 are provided at the bottom wall 801a of cassette 800 to receive interface pins 506 of microfluidic device 500. Sockets 802 are connected to electrical interfaces 808 and 810 built on the sidewalls of cassette 800. Interface 810 can be used for high voltage connection (e.g., used to apply voltages to electrodes 512a–512d), and interface 808 can be used for various measurement and controlling signals.

photo sensor 804 is mounted on a sidewall of cassette 800 for photo detection. Optical filter 806 is used to block the excitation and the scattering light, and to pass the emission wavelength from the sample excited by the laser in the separation channel 504. Four setscrews 818 are provided at four corners of cassette 800 to allow cassette 800 to be assembled with other components, or be secured on a support frame. Cassette 800 can serve as an interface between the microfluidic device 500 and external components with a convenient "plug-and-play" design. A component that cannot fit within microfluidic device 500 (e.g., due to its size, cost, or compatibility) can be placed in cassette 800. Such components may include a microprocessor, a high power laser source, a photo sensor, and additional optical parts. The cassette structure provides an easy way for microstructure interfacing with structures that can be more easily handled by a user, and makes the detections and controls as close as possible to the microstructure, so that detection signal loss due to transmission is decreased as less as possible and the microsystem performance is increased.

Integrated microfluidic system 900 allows miniaturization of chemical, biological, and medical analytical systems. An advantage of using microfluidic system 900 is that smaller sample and reagent volumes are required, better system portability and disposability. Another advantage is that the microstructures of microfluidic system 900 are fabricated by casting liquid polymers or resins. It is not necessary to use bonding procedures that were used in traditional microfabrication methods. By using casting techniques, microstructures having a variety of shapes and sizes can be achieved. The microstructures can have features with high aspect ratios (i.e., very narrow or small in one dimension as compared to another dimension). The microdevice body 501 can be fabricated as a single structure. There is no liquid leakage from the device and between the microstructures inside the device, as may occur if the microstructure body 501 was fabricated by binding different components. Using casting techniques to fabricate microdevice body 501 increases the quality and reliability of the microfluidic system 900, simplifies the fabrication process, and decreases the product defect rate. When mass-produced, the cost of microfluidic device 500 may be lower compared to cassette 800. Microfluidic device 500 (which is made of polymer or resin, and can be made cheaper) wears out earlier than cassette 800 (which can be made of steel or plastic, and is likely more expensive). Using the plug-and-play approach, it is possible to dispose microfluidic device 500 after repeated usage while retaining cassette 800 for later use.

The techniques for fabricating multi-chamber device 100 and multi-channel device 400 can be used to fabricate complicated Microsystems, in additional to microfluidic device 500.

Using liquid polymers and resins to fabricate microdevice body 501 has the advantage of low cost and low toxicity. Some polymers and resins are transparent from the visible to the near ultraviolet wavelength, which makes them suitable for fluorescence, chromatographic, emission, absorption, and other spectroscopic detection. By integrating electrodes into the channels and chambers of microdevice body 501, electrochemical detection and bioimpedance measurements can be performed. Polymers and resins have the advantage of chemical inertness, versatile surface chemistry, and mechanical flexibility and durability.

The casting techniques described herein for fabricating microstructures can be used in many different applications, including analytical chemistry, biological diagnosis, medical diagnosis, food testing, environment testing, biodefence, and drug detection and screening. Microsystems incorporating microstructures fabricated using the casting techniques can be used in microsensors and microtransducers that are useful for industrial measurement and control. The casting techniques can also be used to create a variety of MEMS devices.

Although some examples have been discussed above, other implementation and applications are also within the scope of the following claims. For example, in FIG. 13, instead of using a photo sensor 804 coupled to waveguide 502, an embedded photo sensor with sufficient sensitivity can be placed near the detection region 529 to detect the fluorescence emission from fluorescent tags bound to the DNA fragments. A lens may be required to focus the fluorescence emission to the embedded photo sensor. Microfluidic system 900, in addition to being used to analyze DNA fragments, can be used to analyze other types of analytes, including proteins and electrolytes. The DNA fragments can be combined with UV tags that emit light when illuminated with ultraviolet (UV) light. Diode laser 530 may emit UV light suitable for exciting the UV tags.

Fabrication of the microstructure devices using materials that change from solid state to liquid state in response to temperature changes may be performed under controlled environments that have lower temperatures when casting the microstructure device so that the mold components remain in solid state when the casting process is performed. Some materials may be in solid state under a particular atmospheric pressure, and in liquid or vapor state in another atmospheric pressure. Fabrication of the microstructure devices using such materials may be performed under controlled environments that have a higher atmospheric pressure when casting the microstructure device so that the mold components remain in solid state when the casting process is performed. A material that changes from liquid state to solid state Upon exposure to ultraviolet light may also be used to fabricate the mold components. Microfluidic system 900 may be used for different types of electrophoretic analysis in additional to analyzing DNA samples. Microfluidic system 900 may also be used for DNA microarray analysis with an array chip integrated inside a chamber.

The method of fabricating microstructure body 501 can be used to fabricate microstructures used in applications other than microfluidic systems. The technique of assembling a device mold and casting a microstructure body from the device mold can be used to fabricate any micron scale integrated system. Accordingly, other embodiments are within the scope of the following claims.

What is claimed is:

1. A method of fabricating a microstructure device, comprising:
   assembling a mold component and a mold body to form a device mold for the microstructure device, the mold component defining a microstructure of the microstructure device, the mold component comprising a reversible material that changes from a solid form to a liquid form or from a liquid form to a solid form depending on the changes in an environment condition;
   casting the microstructure device from the device mold;
   removing the mold component from the microstructure device by applying a centrifugal force to draw the mold component in liquid form away from the microstructure device; and
   releasing the microstructure device from the mold body.

2. The method of claim 1 wherein casting the microstructure device comprises pouring or injecting a liquid polymer into the device mold.

3. The method of claim 2, further comprising combining the liquid polymer with a filler material or reinforcement particles.

4. The method of claim 2 wherein the liquid polymer comprises polyurethane, polydimethylsiloxane, polycarbonate, polypyrrole, resin, Teflon resin, epoxy, polymeric rubber, or polymeric plastic.

5. The method of claim 1 wherein the mold component comprises wax, gel, fusible alloy, eutectic alloy, resin, lipid, or ammnonium salt.

6. The method of claim 1 wherein the mold component has structures having a dimension less than 5 millimeters.

7. The method of claim 1 wherein removing the mold component comprises changing the one or more environment conditions so that the reversible mold component changes from a solid form to a liquid form.

8. A method of fabricating a microstructure device, comprising:
   assembling a mold component and a mold body to form a device maid for the microstructure device, the mold component defining a microstructure of the microstructure device, the mold component comprising a reversible material that changes from a solid form to a liquid form or from a liquid form to a solid form depending on the changes in an environment condition;
   casting the microstructure device from the device mold;
   removing the mold component from the microstructure device by using a suction force to daw the mold component in liquid form away from the microstructure device; and
   releasing the microstructure device from the mold body.

9. A method of fabricating a microstructure device, comprising:
   assembling a mold component and a mold body to form a device mold for the microstructure device;
   casting the microstructure device from the device mold;
   removing the mold component from the microstructure device; and
   releasing the microstructure device from the mold body;
   wherein the mold component comprises a material that changes from a solid form to a gaseous form or from a gaseous form to a solid form depending on changes in one or more environment conditions.

10. The method of claim 9 wherein removing the mold component comprises changing the one or more environment conditions so that the mold component changes from a solid form to a gaseous form.

11. The method of claim 1 wherein the mold component has a shape that is complementary of a structure of the microstructure device after the mold component is removed from the microstructure device.

12. The method of claim 1 wherein the mold component comprises an elongated mold component having a same dimension and shape as a channel in the microstructure device after the mold component is removed from the microstructure device.

13. The method of claim 1, further comprising fabricating the mold component by using a component mold.

14. The method of claim 13 wherein fabricating the mold component comprises pouring a material in a liquid form into the component mold, and changing one or more environment conditions so tat the material changes to a solid or gel form.

15. The method of claim 13 wherein the component mold has a cavity having a shape that is substantially the same as a shape of the mold component the cavity being connected to an exterior of the component mold through an opening, wherein fabricating the mold component comprises injecting a material in a liquid form into the cavity through the opening, and changing one or more environment conditions so that the material changes to a solid or gel form.

16. A method of fabricating a microstructure device, comprising;
   fabricating a mold component by using a component mold that has a cavity having a shape that is substantially the same as a shape of the mold component, wherein fabricating the mold component comprises compressing a material in powder form into the cavity to form the mold component;
   assembling the mold component and a mold body to form a device mold for the microstructure device;
   casting the microstructure device from the device mold;
   removing the mold component from the microstructure device; and
   releasing the microstructure device from the mold body.

17. A method, comprising:
   assembling a set of mold components and a mold body to form a device mold for a microstructure device, the set of mold components including a first mold component that does not contact the mold body and is coupled to the mold body by one or more connecting components;
   casting the microstructure device from the device mold; and
   removing the set of mold components from the microstructure device, including removing the first mold component to form a chamber in the microstructure device.

18. The method of claim 17 wherein casting the microstructure device comprises pouring or injecting a liquid polymer into the device mold.

19. The method of claim 17 wherein the set of mold components comprises a first elongated mold component and a second elongated mold component, the first elongated mold component having a diameter or dimension smaller then the second elongated mold component, the second elongated mold component having an opening which has same dimensions as the cross section of the first elongated mold component, and assembling the device mold comprises inserting the first elongated mold component through the opening in the second elongated mold component to form an intersection.

20. The method of claim 17, wherein the set of mold components comprises an elongated mold component and a cylinder, the cylinder having a passageway with a dimension substantially the same as a dimension of the elongated mold component, and assembling the device mold comprises partially inserting the elongated mold component into the passageway.

21. The method of claim 17 wherein the set of mold components comprises a castable mold component and an elongated mold component, the castable mold component having a shape configured to form a cavity in the microstructure device, the elongated mold component having a shape configured to form a channel in the microstructure device, the castable mold component having a recess structure for receiving an end of the elongated mold component, the recess structure having means to prevent the castable mold component from moving relative to the elongated mold member when the device mold is assembled.

22. The method of claim 21 wherein the elongated mold component has a first end and a second end, the mold body having a side wall with a hole, wherein assembling the device mold comprises inserting the tint end of the elongated mold component into the recess structure of the castable mold component, and inserting the second end of the elongated mold component through the hole of the side wall of the device mold.

23. The method of claim 21 wherein the set of mold components includes a castable mold component having a shape suitable for forming a cavity and an elongated mold component suitable for forming a channel connecting the cavity in the microstructure device, wherein assembling the device mold comprises inserting the elongated mold component through a hole positioned on a side wall of the mold body, the elongated mold component supporting and aligning the castable mold component at a predefined position relative to the mold body.

24. The method of claim 17 wherein the set of mold components comprises a post and a mold component, the post supporting the mold component at a predetermined position relative to the mold body when the device mold is assembled.

25. A method of fabricating a microstructure device, comprising:
   fabricating a device mold by connecting a set of mold components to a mold body and connecting a set of functional components to the mold body, the mold components defining microstructures of the microstructure device, the mold component comprising a reversible material that changes from a solid form to a liquid form or from a liquid form to a solid form depending on the changes in an environment condition;
   casting the microstructure device from the device mold; and
   removing the set of mold components from the microstructure device while retaining the functional components in the microstructure device, wherein removing the mold components comprises applying a centrifugal force to draw the mold components in liquid form away from the microstructure device.

26. The method of claim 25 wherein casting the microstructure device comprises pouring or injection a liquid polymer into the device mold.

27. The method of claim 25 wherein the set of mold components comprises a castable mold component, the set of functional components comprises an electrode having a tip,
   wherein fabricating the device mold comprises embedding a tip of the electrode into one of the castable mold components so that the tip of the electrode is surrounded by the castable mold component,
   wherein removing the castable mold component from the micro structure device exposes the tip of the electrode to a cavity in the microstructure device.

28. The method of claim 25, wherein the set of mold components comprises an elongated mold component, the set of functional components comprises an electrode having a structure that defines a hole,
   wherein fabricating the device mold comprises inserting the elongated mold component through the hole in the electrode.

29. The method of claim 25 wherein the set of mold components comprises a mold component that defines a conduit in the microstructure device, the method further comprising coating a surface of the conduit with a material having a refractive index lower than a refractive index of a liquid material used for filling the conduit.

30. The method of claim 17 in which removing the set of mold components comprises removing the connecting components to form one or more channels that are connected to the chamber.

31. The method of claim 17 wherein assembling the set of mold components comprises inserting an end of one of the connecting components into a recess structure of the first mold component, the recess structure having means to prevent the first mold component from moving relative to the connecting component when the device mold is assembled.

32. The method of claim 8 wherein casting the microstructure device comprises pouring or injecting a liquid polymer into the device mold.

33. The method of claim 32, further comprising combining the liquid polymer with a filler material or reinforcement particles.

34. The method of claim 32 wherein the liquid polymer comprises polyurethane, polydimethylsiloxane, polycarbonate, polypyrrole, resin, Teflon resin, epoxy, polymeric rubber, or polymeric plastic.

35. The method of claim 8 wherein the mold component comprises wax, gel, fusible alloy, eutectic alloy, resin, lipid, or ammonium salt.

36. The method of claim 8 wherein the mold component has structures having a dimension less than 5 millimeters.

37. The method of claim 8 wherein removing the mold component comprises changing the one or more environment conditions so that the reversible mold component changes from a solid form to a liquid form.

38. A method of fabricating a microstructure device, comprising:
fabricating a device mold by connecting a set of mold components to a mold body and connecting a set of functional components to the mold body, the mold components defining microstructures of the microstructure device, the mold component comprising a reversible material that changes from a solid form to a liquid form or from a liquid form to a solid form depending on the changes in an environment condition;
casting the microstructure device from the device mold; and
removing the set of mold components from the microstructure device while retaining the functional components in the microstructure device, wherein removing the mold component comprises using a suction force to draw the mold component in liquid form away from the microstructure device.

39. The method of claim 38 wherein casting the microstructure device comprises pouring or injection a liquid polymer into the device mold.

40. The method of claim 38 wherein the set of mold components comprises a castable mold component.

41. The method of claim 40 wherein the set of functional components comprises an electrode having a tip.

42. The method of claim 41 wherein fabricating the device mold comprises embedding a tip of the electrode into one of the castable mold components so that the tip of the electrode is surrounded by the castable mold component.

43. The method of claim 42 wherein removing the castable mold component from the microstructure device exposes the tip of the electrode to a cavity in the microstructure device.

44. The method of claim 38 wherein the set of mold components comprises an elongated mold component.

45. The method of claim 44 wherein the set of functional components comprises an electrode having a structure that defines a hole.

46. The method of claim 45 wherein fabricating the device mold comprises inserting the elongated mold component through the bole in the electrode.

47. The method of claim 38 wherein the set of mold components comprises a mold component that defines a conduit in the microstructure device.

48. The method of claim 47, further comprising coating a surface of the conduit with a material having a refractive index lower than a refractive index of a liquid material used for filling the conduit.

* * * * *